United States Patent
Semenkovich et al.

(10) Patent No.: US 8,337,835 B2
(45) Date of Patent: Dec. 25, 2012

(54) USE OF AN ENDOGENOUS LIGAND FOR PEROXISOME PROLIFERATOR ACTIVATED RECEPTOR ALPHA TO TREAT LIVER DISORDERS

(75) Inventors: Clay F. Semenkovich, Ladue, MO (US); Manu V. Chakravarthy, Scotch Plains, NJ (US); John W. Turk, Eureka, MO (US)

(73) Assignee: Washington University, St. Louis, MO (US)

( * ) Notice: Subject to any disclaimer, the term of this patent is extended or adjusted under 35 U.S.C. 154(b) by 85 days.

(21) Appl. No.: 12/758,523

(22) Filed: Apr. 12, 2010

(65) Prior Publication Data
US 2010/0261676 A1      Oct. 14, 2010

Related U.S. Application Data

(60) Provisional application No. 61/168,446, filed on Apr. 10, 2009.

(51) Int. Cl.
  A61K 38/44    (2006.01)
  A61K 31/685   (2006.01)
  G01N 33/48    (2006.01)
  G01N 33/92    (2006.01)
  A01N 43/42    (2006.01)
(52) U.S. Cl. ............. 424/94.4; 436/63; 436/71; 514/78; 514/313; 514/297
(58) Field of Classification Search .......... 424/94.4; 436/63, 71; 514/78, 313, 297
See application file for complete search history.

(56) References Cited

U.S. PATENT DOCUMENTS

| 7,301,033 B2 | 11/2007 | Yamazaki et al. |
| 7,442,796 B2 | 10/2008 | Sharma et al. |
| 2002/0103225 A1* | 8/2002 | Curatolo et al. ............. 514/313 |
| 2006/0172429 A1* | 8/2006 | Nilsson et al. ................ 436/71 |
| 2007/0014841 A1* | 1/2007 | Martin et al. ................ 424/450 |
| 2007/0015807 A1* | 1/2007 | Aslanian et al. ............ 514/397 |
| 2008/0254017 A1* | 10/2008 | Kane et al. ................. 424/94.4 |

FOREIGN PATENT DOCUMENTS

| EP | 0209038 A1 | 1/1987 |
| WO | 2004039430 A2 | 5/2004 |
| WO | 2006006832 A1 | 1/2006 |

OTHER PUBLICATIONS

Kuboi et al., "Refolding of Carbonic Anhydrase Assisted by 1-Palmitoyl-2-oleoyl-sn-glycero-3-phosphocholine Liposomes" in Biotechnol. Prog. 1997, 13, 828-836.*

Akbiyik, F., et al., "Ligand-induced expression of peroxisome proliferator activated receptor α and activation of fatty acid oxidation enzymes in fatty liver," Eur J Clin Invest, 34(6):429-435 (2004).

(Continued)

*Primary Examiner* — Blessing Fubara
(74) *Attorney, Agent, or Firm* — Senniger Powers LLP

(57) ABSTRACT

Compositions comprising the peroxisome proliferator-activated receptor alpha (PPARα)-ligand 1-palmitoyl-2-oleoyl-sn-glycerol-3-phosphocholine (16:0/18:1-GPC) are disclosed. These compositions may be used for the prophylaxis and treatment of PPARα-related liver disorders including, but not necessarily limited to, fatty liver disease, to lower lipid and triglyceride levels, and to increase high density lipoprotein levels in animals. Foods modified with 1-palmitoyl-2-oleoyl-sn-glycerol-3-phosphocholine (16:0/18:1GPC) may be used to improve the metabolism of animals.

8 Claims, 12 Drawing Sheets

OTHER PUBLICATIONS

Auwerx et al., "Regulation of Triglyceride Metabolism by PPARs: Fibrates and Thiazolidinediones have Distinct Effects," J Atherosclerosis and Thrombosis, 3(2): 81-89 (1996).

Ayers et al., "Continuous nucleocytoplasmic shuttling underlies transcriptional activation of PPARgamma by FABP4," Biochemistry, 46:6744-6752 (2007).

Barter, et al., "Is there a role for fibrates in the management of dyslipidemia in the metabolic syndrome?" Arterioscler Thromb Vasc Biol, 28:39-46 (2008).

Bensinger, et al., "Integration of metabolism and inflammation by lipid-activated nuclear receptors," Nature, 454:470-477 (2008).

Benthem, L., et al. "Excess portal venous long-chain fatty acids induce syndrome X via HPA axis and sympathetic activation," Am J Physiol Endocrinol Metab, 279:E1286-E1293 (2000).

Bernal-Mizrachi et al., "Dexamethasone induction of hypertension and diabetes is PPARalpha-dependent in LDL receptor-null mice," Nat Med. 9:1069-1075 (2003).

Billas et al., "Crystal structure of the ligand-binding domain of the ultraspiracle protein USP, the ortholog of retinoid X receptors in insects," J Biol Chem, 276:7465-7474 (2001).

Cantafora, A., et al., "Effect of intravenous polyunsaturated phosphatidylcholine infusion on insulin receptor processing and lipid composition of erythrocytes in patients with liver cirrhosis," Eur J Clin Invest, 22:777-782 (1992).

Chakravarthy et al., "New hepatic fat activates PPARalpha to maintain glucose, lipid, and cholesterol homeostasis," Cell Metab 1, 309-322 (2005).

Chakravarthy et al., "Brain fatty acid synthase activates PPARalpha to maintain energy homeostasis," J Clin Invest, 117:2539-2552 (2007).

Clayton et al., "The structure of the ultraspiracle ligand-binding domain reveals a nuclear receptor locked in an inactive conformation," PNAS USA, 98:1549-1554 (2001).

Cuzzocrea et al., "Role of endogenous and exogenous ligands for the peroxisome proliferators activated receptors alpha (PPARalpha) in the development of inflammatory bowel disease in mice," Lab Invest, 84:1643-1654 (2004).

Davies et al. "Oxidized alkyl phospholipids are specific, high affinity peroxisome proliferator-activated receptor gamma ligands and agonists," J Biol Chem, 276:16015-16023 (2001).

Delerive et al., "Oxidized phospholipids activate PPARalpha in a phospholipase A2-dependent manner," FEBS Letters, 471:34-38 (2000).

Dreyer, et al., "Control of the Peroxisomal .beta.-Oxidation Pathway by a Novel Family of Nuclear Hormone Receptors," Cell, 68:879-887 (1992).

Fischer et al., "Peroxisome Proliferator-activated Receptor a (PPARα) Agonist Treatment Reverses PPARα Dysfunction and Abnormalities in Hepatic Lipid Metabolism in Ethanol-fed Mice," J. Biol Chem, 278(30):27997-28004 (2003).

Forman et al., "Hypolipidemic drugs, polyunsaturated fatty acids, and eicosanoids are ligands for peroxisome proliferator-activated receptors alpha and delta," PNAS USA, 94:4312-4317 (1997).

Forman, B.M., "Are those phospholipids in your pocket?" Cell Metab 1, 153-155 (2005).

Fruchart, et al., "Peroxisome proliferator-activated receptor-alpha activators regulate genes governing lipoprotein metabolism, vascular inflammation and atherosclerosis," Current Opinion in Lipidology, 10:245-257 (1999).

Gervois et al., "Regulation of lipid and lipoprotein metabolism by PPAR activators," Clin. Chem. Lab. Med. 38: 3-11 (2000).

Ginsberg, H. N., et al., "The insulin resistance syndrome: impact on lipoprotein metabolism and. Atherothrombosis," J. Cardiovasc. Risk 7:325-331 (2000).

Gonzalez et al., "Mechanism of Action of the Nongenotoxic Peroxisome Proliferators: Role of the Peroxisome Proliferator-Activated Receptor .alpha," Journal of the National Cancer Institute, 90(22):1702-1709 (1998).

Guo et al., "Enzymatic modification of phospholipids for functional applications and human nutrition," Biotechnology Advances, 23:203-259 (2005).

Haffner, S. M., "Diabetes, Hyperlipidemia, and Coronary Artery Disease," Am. J. Cardiol., 83:17F-21F (1999).

Henneberry et al., "The major sites of cellular phospholipid synthesis and molecular determinants of fatty Acid and lipid head group specificity," Mol Biol Cell, 13:3148-3161 (2002).

Henry, S.M., et al., "Evidence for a unique profile of phosphatidylcholine synthesis in late mitotic cells," J Cell Biol, 97:166-172 (1983).

Hsu and Turk, "Structural determination of sphingomyelin by tandem mass spectrometry with electrospray ionization," J Am Soc Mass Spectrom 11, pp. 437-449 (2000).

Hsu and Turk, "Electrospray ionization/tandem quadrupole mass spectrometric studies on phosphatidylcholines: the fragmentation processes," J Am Soc Mass Spectrom, 14:352-363 (2003).

Hsu et al., "Formation of lithiated adducts of glycerophosphocholine lipids facilitates their identification by electrospray ionization tandem mass spectrometry," J Am Soc Mass Spectrom, 9:516-526 (1998).

Hsu et al., "Characterization of alkylacyl, alk-1-enylacyl and lyso subclasses of glycerophosphocholine by tandem quadrupole mass spectrometry with electrospray ionization," J Mass Spectrom, 38:752-763 (2003).

Hunt et al., "Developmental variation in whole human lung phosphatidylcholine molecular species: a comparison with guinea pig and rat," Early Hum Dev, 25:157-171 (1991).

Hunt et al., "Highly saturated endonuclear phosphatidylcholine is synthesized in situ and colocated with CDP-choline pathway enzymes," J Biol Chem, 276:8492-8499 (2001).

Hunt et al., "Phospholipid composition of neonatal guinea pig liver and plasma: effect of postnatal food restriction," Lipids, 31:489-495 (1996).

Issemann, et al., "Activation of a member of the steroid hormone receptor superfamily by peroxisome proliferators," Nature, 347:645-650 (1990).

Kent, C., "Regulatory enzymes of phosphatidylcholine biosynthesis: a personal perspective," Biochim Biophys Acta, 1733:53-66 (2005).

Kliewer et al., "Fatty acids and eicosanoids regulate gene expression through direct interactions with peroxisome proliferator-activated receptors alpha and gamma," PNAS USA, 94:4318-432 (1997).

Krey et al., "Fatty acids, eicosanoids, and hypolipidemic agents identified as ligands of peroxisome proliferator-activated receptors by coactivator-dependent receptor ligand assay," Mol Endocrinol, 11:779-791 (1997).

Krylova et al. "Structural analyses reveal phosphatidyl inositols as ligands for the NR5 orphan receptors SF-1 and LRH-1," Cell, 120:343-355 (2005).

Lee et al., "Role for peroxisome proliferator-activated receptor alpha in oxidized phospholipid-induced synthesis of monocyte chemotactic protein-1 and interleukin-8 by endothelial cells," Circ Res, 87:516-521 (2000).

Li et al., Crystallographic identification and functional characterization of phospholipids as ligands for the orphan nuclear receptor steroidogenic factor-1, Mol Cell, 17:491-502 (2005).

Lodhi et al., "Gapex-5, a Rab31 guanine nucleotide exchange factor that regulates Glut4 trafficking in adipocytes," Cell Metab. 5:59-72 (2007).

Mansbach, C.M., et al., "Portal transport of long acyl chain lipids: effect of phosphatidylcholine and low infusion rates," Am J Physiol, 264:G1082-G1089 (1993).

Newberry et al., "Decreased hepatic triglyceride accumulation and altered fatty acid uptake in mice with deletion of the liver fatty acid-binding protein gene," J Biol Chem, 278:51664-51672 (2003).

Nowatzke et al., "Mass spectrometric evidence that agents that cause loss of Ca2+ from intracellular compartments induce hydrolysis of arachidonic acid from pancreatic islet membrane phospholipids by a mechanism that does not require a rise in cytosolic Ca2+ concentration," Endocrinology, 139:4073-4085 (1998).

Ortlund et al., "Modulation of human nuclear receptor LRH-1 activity by phospholipids and SHP," Nat Struct Mol Biol, 12:357-363 (2005).

Panigrahy et al., "PPARalpha agonist fenofibrate suppresses tumor growth through direct and indirect angiogenesis inhibition," PNAS USA, 105:985-990 (2008).

Pineda et al., "Peroxisome proliferator-activated receptor alpha in metabolic disease, inflammation, atherosclerosis and aging," Current Opinion in Lipidology, 10:151-159 (1999).

Pioszak et al., "Molecular recognition of parathyroid hormone by its G protein-coupled receptor," PNAS USA, 105:5034-5039 (2008).

Reddy et al., "Peroxisomal beta-oxidation and peroxisome proliferator-activated receptor alpha: an adaptive metabolic system," Annu Rev Nutr, 21:193-230 (2001).

Ridgway, et al., "Regulation of the CDP-choline pathway by sterol regulatory element binding proteins involves transcriptional and post-transcriptional mechanisms," Biochem J, 372:811-819 (2003).

Riserus et al., "Activation of peroxisome proliferator-activated receptor (PPAR)delta promotes reversal of multiple metabolic abnormalities, reduces oxidative stress, and increases fatty acid oxidation in moderately obese men," Diabetes, 57:332-339 (2008).

Robins et al., "PPAR.alpha. ligands and clinical trials: cardiovascular risk reduction with fibrates," Journal of Cardiovascular Risk, 8(4):195-201 (2001).

Schoonjans et al., "The peroxisome proliferator activated receptors (PPARs) and their effects on lipid metabolism and adipocyte differentiation," Biochimica et Biophysica Acta, 1302:93-109 (1996).

Semenkovich, C.F. "Regulation of fatty acid synthase (FAS)," Prog Lipid Res, 36:43-53 (1997).

Seo et al., "PPAR agonists treatment is effective in a nonalcoholic fatty liver disease animal model by modulating fatty-acid metabolic enzymes," J. Gastroenterology and Hepatology, 23(1):102-108 (2008).

Shah et al., "Peroxisome proliferator-activated receptor alpha regulates a microRNA-mediated signaling cascade responsible for hepatocellular proliferation," Mol Cell Biol, 27:4238-424 (2007).

Shi et al., "The peroxisome proliferator-activated receptor delta, an integrator of transcriptional repression and nuclear receptor signaling," PNAS USA, 99:2613-2618 (2002).

Staels et al., "Role of PPAR in the Pharmacological Regulation of Lipoprotein Metabolism by Fibrates and Thiazolidinediones," Current Pharmaceutical Design, 3(1):1-14 (1997)—Abstract Only.

Straus and Glass "Anti-inflammatory actions of PPAR ligands: new insights on cellular and molecular mechanisms," Trends Immunol, 28:551-558 (2007).

Stremmel, et al., "Phosphatidylcholine for steroid-refractory chronic ulcerative colitis: a randomized trial," Ann Intern Med, 147:603-610 (2007).

Strubbe et al., "Hepatic portal vein cannulation for infusion and blood sampling in freely moving rats," Physiol Behavior, 65:885-887 (1999).

Tanaka et al., "PPARalpha activation is essential for HCV core protein-induced hepatic steatosis and hepatocellular carcinoma in mice," J Clin Invest, 118:683-694 (2008).

Tordjman, K., et al., "PPARalpha suppresses insulin secretion and induces UCP2 in insulinoma cells." J Lipid Res, 43:936-943 (2002).

Treede et al., "Anti-inflammatory effects of phosphatidylcholine," J Biol Chem, 282:27155-27164 (2007).

Tzagournis, M. "Triglycerides in clinical medicine; A review," American Journal of Clinical Nutrition, 31:1437-1452 (1978).

Vamecq et al., "Medical significance of peroxisome proliferator-activated receptors," The Lancet, 354:141-148 (1999).

van Nieuwenhuyzen "Lecithin production and properties," J Am Oil Chem Soc, 53:425-427 (1976).

Weihrauch et al., "The phospholipids content of foods," J Am Oil Chem Soc, 60(12):1971-1978 (1983).

Willson, et al., "The PPARs: From Orphan Receptors to Drug Discovery," Journal of Medicinal Chemistry, 43 (4):527-550 (2000).

Wiser, et al., "Increased sensitivity in antigen detection during immunoblot analysis resulting from antigen enrichment via immunoprecipitation," Analytical Biochemistry, 155(1):71-77 (1986).

Yki-Jarvinen, H. "Thiazolidinediones," N Engl J Med, 351:1106-1118 (2004).

Yu et al., "Differential activation of peroxisome proliferator-activated receptors by eicosanoids," J Biol Chem, 270:23975-23983 (1995).

Zhao et al., "Identification and characterization of a major liver lysophosphatidylcholine acyltransferase," J Biol Chem, 283:8258-8265 (2008).

Zomer et al., "Pristanic acid and phytanic acid: naturally occurring ligands for the nuclear receptor peroxisome proliferator-activated receptor α," J Lipid Res, 41(11):1801-1807 (2000).

Nuclear receptors Nomenclature Committee, "A Unified Nomenclature System for the Nuclear Receptor Superfamily," Letter to the Editor, Cell, 97:161-163 (1999).

* cited by examiner

SEQUENCE LISTING

```
<160> NUMBER OF SEQ ID NOS: 8

<210> SEQ ID NO 1
<211> LENGTH: 25
<212> TYPE: RNA
<213> ORGANISM: Mus musculus

<400> SEQUENCE: 1
ggaggagcaa caauguggga cuaua                                         25

<210> SEQ ID NO 2
<211> LENGTH: 25
<212> TYPE: RNA
<213> ORGANISM: Mus musculus

<400> SEQUENCE: 2
```
uggcagugau uggaggacca ccuuu                                    25

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3
tgctcatctt ctactgccct acag                                     24

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
agagtcccag ggcacataaa ag                                       22

<210> SEQ ID NO 5
<211> LENGTH: 26
<212> TYPE: DNA
<213> ORGANISM: Artificial Sequence
<220> FEATURE:
<223> OTHER INFORMATION: Probe

<400> SEQUENCE: 5
cacggaggag gcaccatact ggacat                                   26

<210> SEQ ID NO 6
<211> LENGTH: 19
<212> TYPE: DNA
<213> ORGANISM: Artificial Sequence
<220> FEATURE:
<223> OTHER INFORMATION: Primer

<400> SEQUENCE: 6
tgctggacgg tcccttctc                                           19

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
atccatgagg gtactcttcc aact                                     24

<210> SEQ ID NO 8
<211> LENGTH: 28
<212> TYPE: DNA
<213> ORGANISM: Artificial Sequence
<220> FEATURE:
<223> OTHER INFORMATION: Probe

<400> SEQUENCE: 8
cccttaatgc aaggatactg ggaatggc                                 28

USE OF AN ENDOGENOUS LIGAND FOR PEROXISOME PROLIFERATOR ACTIVATED RECEPTOR ALPHA TO TREAT LIVER DISORDERS

CROSS REFERENCE TO RELATED APPLICATIONS

This application claims the benefit of U.S. Patent Application Ser. No. 61/168,446, which was filed Apr. 10, 2009, and which is hereby incorporated herein by reference in its entirety.

STATEMENT OF GOVERNMENT RIGHTS

This invention was made with Government support under grant number R01DK076729 awarded by the National Institutes of Health. The Government has certain rights in the invention.

FIELD OF THE INVENTION

The present invention generally relates to compositions comprising a peroxisome proliferator-activated receptor alpha (PPARα) ligand and methods of using the same for the diagnosis and treatment of a PPARα-related liver disorder in a mammal.

BACKGROUND

PPAR is known as one of the nuclear receptor families and is known to have three subtypes (alpha, gamma, and delta) (Nature, 347, 645-650, 1990; Cell, 68, pp 879-887, 1992; Cell, 97, pp 161-163, 1999; Biochim. Biophys. Acta., 1302, pp 93-109, 1996; and Journal of Medicinal Chemistry, 43, pp 527-550, 2000). Each receptor appears to modulate pathways at the interface between intermediary metabolism and inflammation, making them physiologically and clinically relevant (Nature 454, 470-477, 2008). Therefore, PPARs are targets of drugs in use and in development to treat disease, and they modulate metabolic and inflammatory pathways by responding to nutritional signals through ligand activation of transcription.

PPARα is activated by fibrate drugs to lower triglycerides and raise HDL (Arterioscler Thromb Vasc Biol 28, 39-46, 2008). PPARγ is targeted by glitazones to treat diabetes (N Engl J Med 351, 1106-1118, 2004), and pharmacological activation of PPARδ appears to improve several metabolic parameters in humans (Diabetes 57, 332-339, 2008). PPARs are ligand-activated receptors that heterodimerize with RXR, bind to response elements in target genes, and alter co-activator/co-repressor dynamics to induce transcription. Fatty acids, especially polyunsaturated ones, are thought to be preferred PPAR ligands, but a wide variety of lipids (Proc Natl Acad Sci USA 94, 4312-4317, 1997; Proc Natl Acad Sci USA 94, 4318-4323, 1997; Mol Endocrinol 11, 779-791, 1997; J Biol Chem 270, 23975-23983, 1995) have been implicated in PPAR activation including saturated fatty acids, fatty acyl-CoA species, eicosanoids (including prostaglandins, leukotrienes, and HETEs), oxidized fatty acids, and oxidized phospholipids. PPARα is activated by drugs to treat human disorders of lipid metabolism (WO 2006-006832, U.S. Pat. No. 7,301,033, European Journal of Clinical Investigation, 34, 429-435, 2004). Of the three subtypes of PPAR, PPARα is mainly expressed at high levels in liver where it promotes fatty acid oxidation, ketogenesis, lipid transport, and gluconeogenesis (Nat Med 9, pp. 1069-1075, 2003; Annu Rev Nutr 21, pp. 193-230, 2001).

Even though some naturally occurring fatty acids such as pristanic acid, phytanic acid, palmitic acid, oleic acid, linoleic acid, and arachidonic acid have been characterized as endogenous ligands of PPARα, it has been reported that some of these naturally occurring free fatty acids which act as ligands of PPARα do not bind with sufficient affinity to PPARα in comparison to a prototypical synthetic fibrate agonist, Wy14, 643, within the context of alcohol-induced fatty liver disease. (Journal of Lipid Research, 41(11) 1801-1807, 2000; Molecular Endocrinology 11, 779-791, 1997; European Journal of Clinical Investigation, 34, 429-435, 2004; Journal of Biological Chemistry, 278 (30), 27997-28004, 2003.) Moreover, none of these naturally occurring free fatty acids are authentic endogenous PPARα ligands because they do not occupy the nuclear receptor binding site in vivo while the receptor is actively driving transcription. Therefore, such free fatty acids are not the most physiologically relevant tissue-specific endogenous PPARα ligands. Furthermore, to date, a physiologically relevant and naturally occurring endogenous tissue-specific phosphatidylcholine ligand that selectively binds to PPARα has not been disclosed as a treatment for fatty liver disease.

Fatty liver disease is one of the most common causes of chronic liver disorders. (Journal of Gastroenterology and Hepatology, 23, 102-109, 2006.) Although the pathogenesis of human fatty liver disease is not completely understood, it is generally acknowledged that the disease status is potentiated by an increased influx and accumulation of free fatty acids in the liver. (European Journal of Clinical Investigation, 34, 429-435, 2004.) The increased fatty acid input to the liver is counterbalanced with fatty acid oxidation systems to prevent fat accumulation and PPARα may play a key role in this step by controlling fatty acid oxidation in all potential sources. (European Journal of Clinical Investigation, 34, 429-435, 2004). U.S. Pat. No. 7,442,796 discloses that a substantial fraction of the population is affected by fatty liver disease, also known as nonalcoholic fatty liver disease (NAFLD), which includes nonalcoholic steatohepatitis (NASH). NASH is often associated with obesity and diabetes. Fatty liver disease or hepatic steatosis, the presence of droplets of triglycerides with hepatocytes, predisposes the liver to chronic inflammation (detected in biopsy samples as infiltration of inflammatory leukocytes), which can lead to fibrosis and cirrhosis. Fatty liver disease is generally detected by observation of elevated serum levels of liver-specific enzymes such as the transaminases ALT and AST, which serve as indices of hepatocyte injury, as well as by presentation of symptoms which include fatigue and pain in the region of the liver, though definitive diagnosis often requires a biopsy. Hepatic gene expression profile encompassing PPARα and some representative enzymes involved in the oxidation of free fatty acids like acyl-CoA oxidase(ACO or AOX); acyl-CoA dehydrogenase, Carnitine Palmitoyl Transferase I and II(CPT-1 and CPT-II), Fatty Acid Binding Protein, Fatty Acid Transport Protein have been reported as being potentially involved in the pathology of fatty liver disease. (Journal of Gastroenterology and Hepatology, 23, 102-109, 2006; European Journal of Clinical Investigation, 34, 429-435, 2004; Journal of Biological Chemistry, 278 (30), 27997-28004, 2003.)

Although PPARα agonists are relatively effective in treating nonalcoholic fatty liver disease, there is still an on-going need for safe and effective treatments for fatty liver disease. (Journal of Gastroenterology and Hepatology, 23, 102-109, 2006; U.S. Pat. No. 7,442,796.) Therefore, treatment of fatty liver disease using a tissue specific naturally occurring authentic endogenous ligand of PPARα would be of value in treating this condition. Furthermore, it is anticipated that amongst other benefits, the delivery of a therapeutically effective PPARα-ligand will eventually lead to the reduction in liver inflammation and fat content, resulting in attenuation, halting, or reversal of the progression of NASH toward fibrosis and cirrhosis.

SUMMARY OF THE INVENTION

Among the various aspects of the present invention is the provision of a naturally occurring, physiologically relevant tissue-specific authentic endogenous PPARα ligand, 1-palmitoyl-2-oleoyl-sn-glycerol-3-phosphocholine (16:0/18:1-GPC) that selectively binds to PPARα for the treatment of a PPARα-related liver disorders including but not necessarily limited to fatty liver disease. Further provided is an isolated PPARα-1-palmitoyl-2-oleoyl-sn-glycerol-3-phosphocholine (16:0/18:1-GPC) receptor-ligand complex from liver cells and an isolated 1-palmitoyl-2-oleoyl-sn-glycerol-3-phosphocholine (16:0/18:1-GPC)-chaperone complex from liver cells for the treatment of a PPARα-related liver disorder including but not necessarily limited to fatty liver disease. Briefly, therefore, the present invention is directed to compositions and methods for the diagnosis and treatment of PPARα-related liver disorders, including but not necessarily limited to fatty liver disease, in a safe and effective manner through the use of an authentic endogenous ligand of PPARα which restores the expression of PPARα-dependent genes.

Thus, one aspect of the present invention is a method of treating a PPARα-related liver disorder, lowering triglyceride levels, and/or elevating high density lipoprotein levels in a mammal. The method comprises administering a therapeutically effective amount of 1-palmitoyl-2-oleoyl-sn-glycerol-3-phosphocholine (16:0/18:1-GPC) to said mammal.

Another aspect of the invention is a method of treating a PPARα-related liver disorder, lowering triglyceride levels, and/or elevating high density lipoprotein levels in a mammal. The method comprises administering a therapeutically effective amount of a 1-palmitoyl-2-oleoyl-sn-glycerol-3-phosphocholine (16:0/18:1-GPC)-chaperone complex to said mammal.

Another aspect of the present invention encompasses a means for determining the presence or absence of PPARα-related liver disorders, including but not necessarily limited to fatty liver disease, which comprises an evaluation of an amount of PPARα-1-palmitoyl-2-oleoyl-sn-glycerol-3-phosphocholine (16:0/18:1-GPC) receptor-ligand complex and amounts of a chaperone, 1-palmitoyl-2-oleoyl-sn-glycerol-3-phosphocholine (16:0/18:1-GPC), and the 1-palmitoyl-2-oleoyl-sn-glycerol-3-phosphocholine (16:0/18:1-GPC)-chaperone complex. This aspect of the invention includes a method of determining presence or absence of a PPARα-related liver disorder in a patient, said method comprising lysing liver cells obtained from the patient to form lysed cells; isolating a PPARα-1-palmitoyl-2-oleoyl-sn-glycerol-3-phosphocholine (16:0/18:1-GPC) receptor-ligand complex from the lysed cells; measuring the amount of the PPARα-1-palmitoyl-2-oleoyl-sn-glycerol-3-phosphocholine (16:0/18:1-GPC) receptor-ligand complex; and determining the presence or absence of a PPARα-related liver disorder based on the amount of the complex.

Another aspect of the invention is a method of determining presence or absence of a PPARα-related liver disorder. The method comprises lysing liver cells obtained from a patient to form lysed cells; isolating a chaperone, 1-palmitoyl-2-oleoyl-sn-glycerol-3-phosphocholine (16:0/18:1-GPC), and a 1-palmitoyl-2-oleoyl-sn-glycerol-3-phosphocholine (16:0/18:1-GPC)-chaperone complex from the lysed cells; measuring the amount of the chaperone, the 1-palmitoyl-2-oleoyl-sn-glycerol-3-phosphocholine (16:0/18:1-GPC), and the 1-palmitoyl-2-oleoyl-sn-glycerol-3-phosphocholine (16:0/18:1-GPC)-chaperone complex; and determining the presence or absence of a PPARα-related liver disorder based on the amounts of the chaperone, the 1-palmitoyl-2-oleoyl-sn-glycerol-3-phosphocholine (16:0/18:1-GPC), and the 1-palmitoyl-2-oleoyl-sn-glycerol-3-phosphocholine (16:0/18:1-GPC)-chaperone complex.

Yet another aspect of the present invention involves the use of the endogenous PPARα ligand, 1-palmitoyl-2-oleoyl-sn-glycerol-3-phosphocholine (16:0/18:1 GPC) to modify foods in order to improve the overall metabolism in a mammalian subject and lowering triglyceride levels in a mammalian subject. Included in this aspect is a method for modifying the 1-palmitoyl-2-oleoyl-sn-glycerol-3-phosphocholine (16:0/18:1-GPC) content of food, said method comprising adding 1-palmitoyl-2-oleoyl-sn-glycerol-3-phosphocholine (16:0/18:1-GPC) to a food product.

Related thereto is another aspect of the invention directed to a method for improving the metabolism of a mammal. The method comprises administering to said mammal a modified food product comprising supplemental 1-palmitoyl-2-oleoyl-sn-glycerol-3-phosphocholine (16:0/18:1-GPC).

Another aspect of the invention is a method of isolating a PPARα-1-palmitoyl-2-oleoyl-sn-glycerol-3-phosphocholine (16:0/18:1-GPC) receptor-ligand complex from a mammalian liver. The method comprises lysing mammalian liver cells to form lysed cells, isolating a PPARα-1-palmitoyl-2-oleoyl-sn-glycerol-3-phosphocholine (16:0/18:1-GPC) receptor-ligand complex from the lysed cells.

Another aspect of the present invention is a liver-specific fatty acid synthase (FAS) knockout mouse within the genetic background of a PPARα-/- null genotype. This aspect includes a method of generating a liver-specific fatty acid synthase (FAS) knockout mouse, said method comprising crossing a liver-specific fatty acid synthase knockout mouse with a PPARα-/- null mouse.

Other objects and features will be in part apparent and in part pointed out hereinafter.

BRIEF DESCRIPTION OF THE DRAWINGS

FIG. 1A illustrates representative PCR genotyping assays for mice wild type at the PPARα locus (lane 4), PPARα heterozygotes (lane 3), and PPARα-deficient mice used for subsequent experiments with fatty acid synthase (FAS) expression (lane 1, WT PPARα-/-) or without FAS expression (lane 2, FASKOL PPARα-/). FIG. 1B illustrates an Immunoblot analysis of liver lysates for wild type (WT) and FASKOL mice on a PPARα null background using FAS (top panel) and actin (bottom panel) antibodies. FIG. 1C graphically illustrates an analysis of Fatty Acid Synthase activity. FIG. 1D graphically illustrates an analysis of the Fatty Acid Synthase substrate malonyl-CoA content. FIG. 1E illustrates an experimental strategy for isolating FLAG-tagged PPARα and detecting the endogenous PPARα ligand. FIG. 1F illustrates immunoprecipitation (IP) and immunoblot (IB) analysis in livers of WT and FASKOL mice on a PPARα null background infected with adenoviruses encoding GFP alone (AdGFP) or FLAG-tagged PPARα (AdFLAG-PPARα).

FIGS. 2A and 2C illustrate representative profiles of GPC species in chow fed WT and FASKOL mice on a PPARα null background infected with AdGFP. FIGS. 2B and 2D illustrate representative profiles of GPC species in chow fed WT and FASKOL mice on a PPARα null background infected with AdFLAG-PPARα. FIGS. 2E and 2G illustrate representative profiles of GPC species in zero fat diet (ZFD) fed WT and FASKOL mice on a PPARα null background infected with AdGFP. FIGS. 2F and 2H illustrate representative profiles of GPC species in zero fat diet (ZFD) fed WT and FASKOL mice on a PPARα null background infected with AdFLAG-PPARα. FIG. 2I graphically illustrates the relative abundance of the mass-to-charge ratio (m/z) 766 ion for the results of experiments illustrated in FIGS. 2A, 2B, 2C, 2D, 2E, 2F, 2G and 2H. Inserts in FIGS. 2B, 2D, 2F, and 2H depict the m/z 766 ion as the specific GPC species that is both PPARα and FAS dependent.

FIG. 3A is a mass spectrometric analysis illustrating the fragmentation pattern upon collisionally-activated dissociation of the ion of m/z 766, which corresponds to the lithiated adduct [MLi$^+$] of 16:0/18:1-GPC. FIG. 3B is a mass spectrometric analysis illustrating the expansion of the mass spectrum in FIG. 3A from m/z 400 to m/z 540, illustrating the relative abundances of ions that represent losses of fatty acid substituents, and indicating that palmitate and oleate are the sn-1 and sn-2 substituents, respectively, of the phosphatidylcholine species. FIG. 3C illustrates a structure of the putative PPARα ligand.

FIGS. 4A, 4B, 4C and 4D are representative ESI/MS/MS scans of GPC species at baseline (time 0) (FIG. 4A), 10 min (FIG. 4B), 30 min (FIG. 4C) and 60 min (FIG. 4D) following an intraperitoneal injection of 50 μg/g Wy14,643 in chow fed WT mice on a PPARα null background injected with AdFLAG-PPARα adenovirus. FIGS. 4E, 4F, 4G and 4H are representative ESI/MS/MS scans of GPC species at baseline (time 0) (FIG. 4E), 10 min (FIG. 4F), 30 min (FIG. 4G) and 60 min (FIG. 4H) following an intraperitoneal injection of 50 μg/g Wy14,643 in ZFD fed mice. FIG. 4I graphically illustrates quantification of the relative abundance of the m/z 766 ion for the independent experiments of FIGS. 4A, 4B, 4C, 4D, 4E, 4F, 4G and 4H. The graph represents mean±SEM from two independent experiments with 4-5 mice in each group per experiment.

FIG. 5A represents a schematic diagram of the modular domain structure of PPARα (top panel). AF, activating function; LBD, ligand binding domain. The two highly conserved cysteine residues (blue) within the DBD of the PPAR family (bottom panel) were mutated to alanine (red). FIG. 5B illustrates immunoblot analysis of Cos-7 cells transfected with empty vector, wild type (WT), or DBD-mutant (ΔDBD) PPARα plasmids using anti-PPARα and proliferating cell nuclear antigen (PCNA) antibodies. Gels are representative of three independent experiments. FIG. 5C illustrates genetic mutations of C119A and C122A of the PPARα gene which disrupt PPARα DNA binding activity. Graphs represent mean±SEM of experiments performed in triplicate. *, $P<0.05$ vs. empty vector. #, $P<0.05$ vs. WT control. FIGS. 5D and 5F are representative ESI/MS/MS scans monitoring neural loss of 189 from lithiated adducts of GPC species in FLAG-eluted hepatic nuclear extracts obtained from chow fed WT and FASKOL mice on a PPARα null background infected with AdGFP adenoviruses. FIGS. 5E and 5G illustrate representative ESI/MS/MS scans monitoring neural loss of 189 from lithiated adducts of GPC species in FLAG-eluted hepatic nuclear extracts obtained from chow fed WT and FASKOL mice on a PPARα null background infected with AdFLAG-$^{ΔDBD}$PPARα adenoviruses. FIG. 5H graphically illustrates quantification of the relative abundance of the m/z 766 ion in response to control and mutant adenoviral injections in W/P (WT on PPARα null background) and F/P (FASKOL on PPARα null background) mice for the independent experiments of FIGS. 5D, 5E, 5F and 5G. Each bar represents the mean±SEM from three independent experiments with 4-6 mice in each group per experiment. *, $P<0.05$ vs. corresponding W/P control. FIGS. 5I, 5J, 5K and 5L are representative neutral loss of 189 ESI/MS scans of GPC species at baseline (time 0) (FIG. 5I), 10 min (FIG. 5J), 30 min (FIG. 5K) and 60 min (FIG. 5L) following intraperitoneal injection of 50 μg/g Wy14,643 in chow fed WT mice on a PPARα null background injected with AdFLAG-$^{ΔDBD}$PPARα adenovirus. Insets in FIG. 5I through FIG. 5L indicate that the ion at m/z 766 (16:0/18:1-GPC) is time-dependently competed away from the DBD defective PPARα with Wy14,643. FIG. 5M graphically illustrates the competitive inhibition data as the relative abundance of the m/z 766 ion in response to Wy14,643 administration in WT mice on a PPARα null background injected with AdFLAG-$^{ΔDBD}$ PPARα adenovirus from independent experiments of FIGS. 5I, 5J, 5K and 5L. Graphs represent mean±SEM from two separate experiments with 3-4 mice in each group per experiment.

FIG. 6A graphically illustrates the effect of Wy14,643, 1-palmitoyl-2-oleoyl-sn-glycerol-3-phosphocholine (16:0/18:1-GPC), and 1-Oleoyl-2-Palmitoyl-sn-Glycero-3-Phosphocholine (18:1/16:0-GPC) on PPARα target gene (ACO and CPT-1) expression by quantitative RT-PCR in Hepa 1-6 cells treated for 24 h. Results are mean±SEM of 9 separate experiments. *, $P<0.05$ compared to control (Ctrl, 80% PBS/20% DMSO). FIG. 6B is a schematic of the Kennedy pathway to generate phosphatidylcholine (PtdCho). CK, choline kinase; CTP, cytosine triphosphate; CCT, CTP phosphocholinecitidyltransferase; DAG, diacyl glycerol; ChPT1, choline phosphotransferase 1; CEPT1, choline-ethanolamine phosphotransferase 1. FIG. 6C graphically illustrates the effect on ChPT1 and CEPT1 mRNA levels normalized to L32 ribosomal mRNA in response to 72 h treatment with corresponding siRNAs and scrambled (Scr) controls in Hepa 1-6 cells. FIG. 6D graphically illustrates the effect of 72 h treatment with scrambled and ChPT1 siRNAs on PPARα target genes (ACO and CPT-1) by RT-PCR normalized to L32 ribosomal mRNA in Hepa 1-6 cells. FIG. 6E graphically illustrates the effect of 72 h treatment with scrambled and CEPT1 siRNAs on ACO and CPT-1 message levels in Hepa 1-6 cells. Expression of ACO and CPT-1 was also assessed 24 h after addition of 50 μM 16:0/18:1-GPC in a subset of Hepa 1-6 cells previously treated with CEPT1 siRNA. mRNA levels are normalized to control L32 ribosomal mRNA. For FIGS. 6C, 6D, and 6E, graphs represent mean±SEM of three separate experiments with each group in triplicate. *, $P<0.05$ compared to scrambled controls. #, $P<0.05$ compared to CEPT1 siRNA treated cells. FIGS. 6F, 6G, 6H graphically illustrate binding of various peptide motifs to the purified PPARα (FIG. 6F), PPARδ (FIG. 6G), and PPARγ (FIG. 6H) ligand binding domains(LBDs) in the presence of 5 μM of the corresponding PPAR agonist or 16:0/18:1-GPC as measured by ALPHASCREEN™ assays. The background signals of either the respective LBDs or the peptides alone, or without addition of the ligand/agonist (no compound), are all less than 800. Results are averages of two separate experiments.

FIG. 7A is a photograph showing an operative field depicting the portal vein (PV) cannulated with a catheter (pv-cath) positioned at the entry site into the liver (lvr). The catheter is intentionally marked in black ink at its proximal tip to enhance visualization. Labels indicate gall bladder (gb), bile duct (bd), inferior vena cava (ivc), and pancreas (pan). FIG. 7B illustrates an intraportal 16:0/18:1-GPC treatment protocol. FIG. 7C illustrates an end of treatment protocol in which liver histological sections were stained with oil red O to visualize neutral lipids (×40 magnification) from wild type (C57/BL6) and PPARα$^{-/-}$ mice treated with 16:0/18:1-GPC or vehicle (Veh). Sections are representative of several animals for each condition. FIG. 7D graphically illustrates quantification of hepatic triglyceride content per unit mass of tissue from vehicle and 16:0/18:1-GPC treated C57/BL6 and PPARα$^{-/-}$ mice. Bars represent mean±SEM of two separate infusion experiments with 5-8 animals per group in each experiment. *, P<0.05 vs. corresponding Veh. #, P<0.05 vs. C57/BL6 controls. FIG. 7E graphically illustrates expression of hepatic acyl-CoA oxidase (ACO) (top panel) and carnitine palmitoyl transferase I (CPT-1) (bottom panel) mRNA by RT-PCR normalized to control L32 ribosomal mRNA following the 16:0/18:1-GPC injections. Data represent mean±SEM of two independent RT-PCR experiments for each gene with 4 mice per genotype per group. *, P<0.05 vs. corresponding Veh. #, P<0.05 vs. C57/BL6 controls. FIG. 7F illustrates a proposed model for the generation of the endogenous PPARα ligand, 1-palmitoyl-2-oleoyl-sn-glycerol-3-phosphocholine (16:0/18:1-GPC) in liver. FAS yields palmitate (C16:0), and 16:0/18:1-GPC is likely generated through the diacylglycerol (DAG) intermediate and the enzymatic activity of CEPT1 either in the ER or the nucleus. Binding of 16:0/18:1-GPC to PPARα in the nucleus activates the transcription machinery (TM) turning on PPARα-dependent genes and affecting hepatic lipid metabolism. ACC, acetyl CoA carboxylase; ER, endoplasmic reticulum.

FIG. 12A graphically illustrates measurement and normalization to tissue weight of the counts of lipids extracted from the cytosolic and nuclear fractions of mouse livers. FIG. 12B graphically illustrates the recovery of the radiolabeled fractions calculated based on radioactive counts obtained at the indicated times normalized to total counts injected per gram of liver. Graphs represent mean±SEM of 3 separate experiments with 3-4 mice per group.

ABBREVIATIONS AND DEFINITIONS

Figure 1:
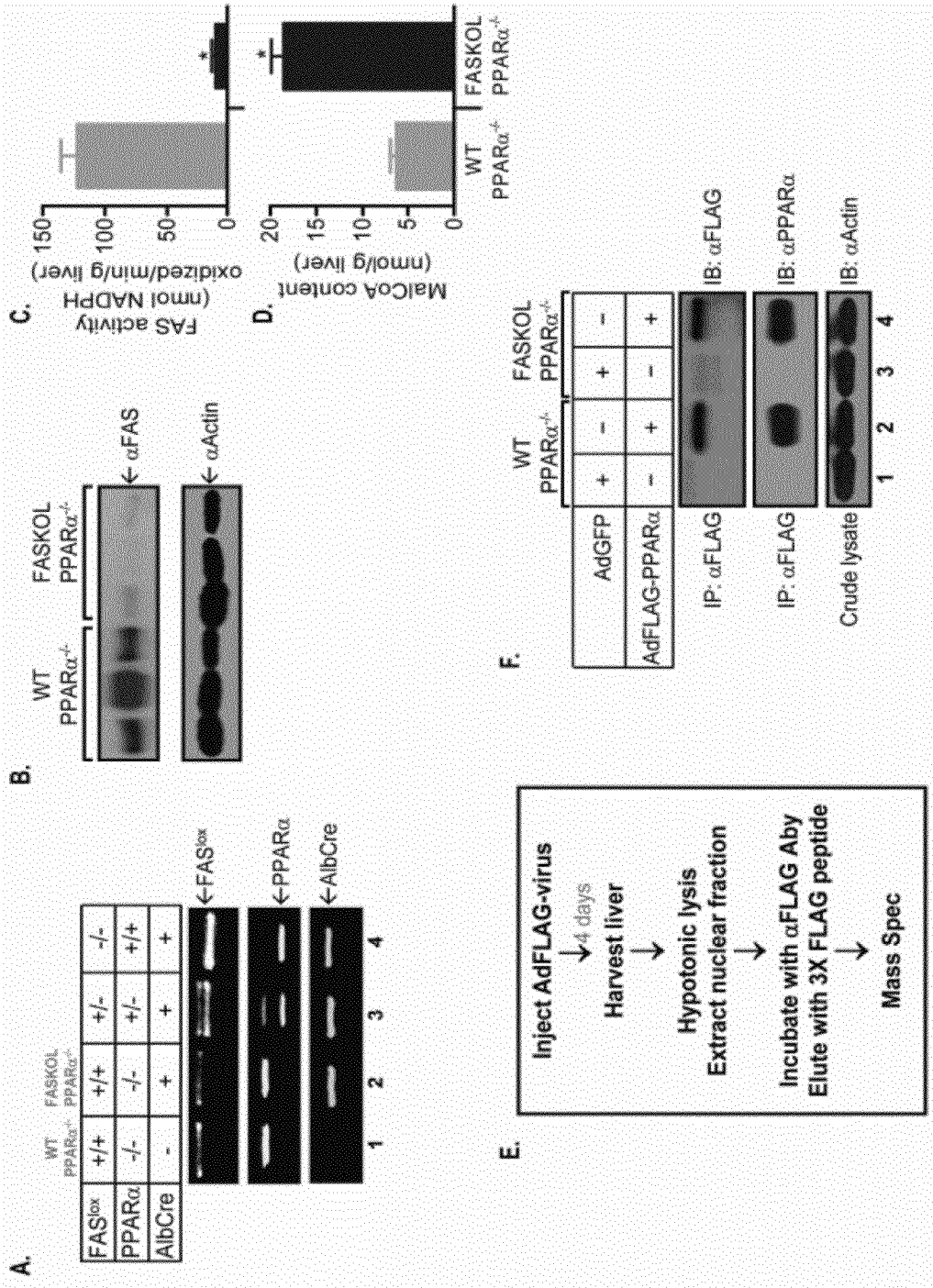
FIG. 1 depicts a generation of liver-specific fatty acid synthase knockout in liver (FASKOL) mice on a PPARα null background and reconstitution of liver PPARα expression.
Figure 2:
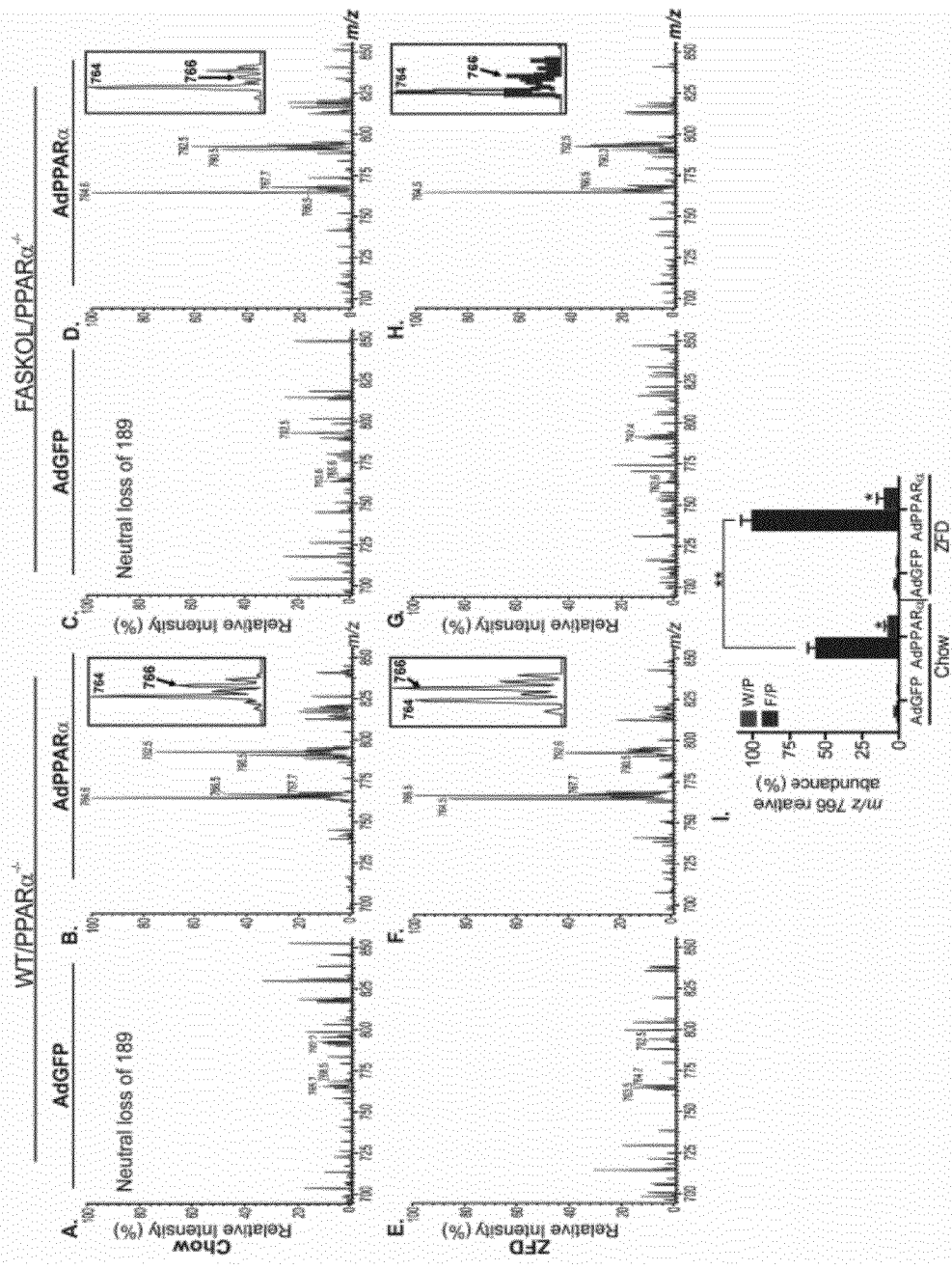
FIG. 2 illustrates mass spectrometric analysis of FLAG®-eluted hepatic nuclear extractase and identification of a glycerophosphocholine (GPC) species in the extracts.
Figure 3:
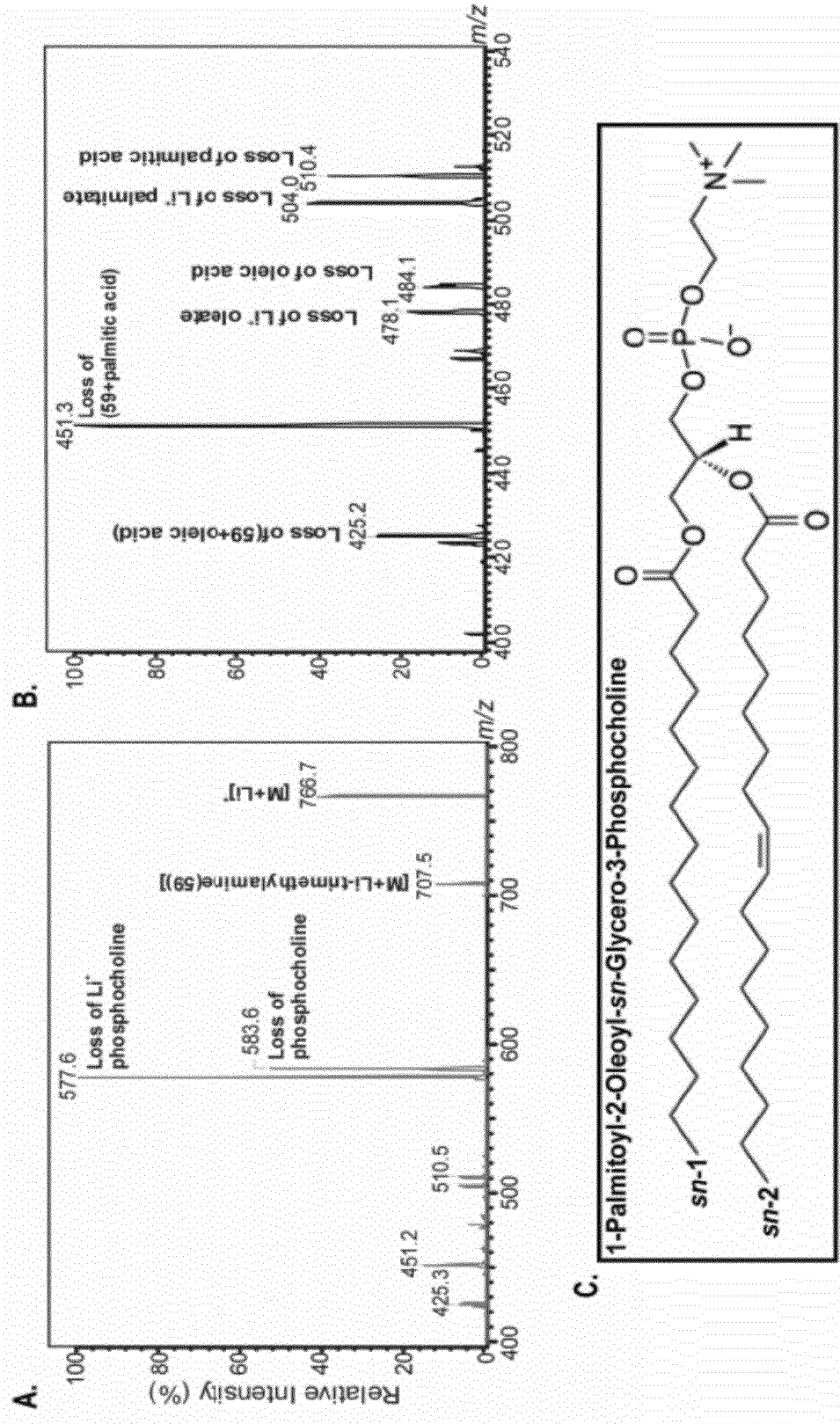
FIG. 3 illustrates the identification of phosphatidylcholine, 1-palmitoyl-2-oleoyl-sn-glycerol-3-phosphocholine (16:0/18:1-GPC) by tandem mass spectrometry.

The following definitions and methods are provided to better define the present invention and to guide those of ordinary skill in the art in the practice of the present invention. Unless otherwise noted, terms are to be understood according to conventional usage by those of ordinary skill in the relevant art.

PPARα refers to peroxisome proliferator-activated receptor alpha.

16:0/18:1-GPC refers to the PPARα ligand, 1-palmitoyl-2-oleoyl-sn-glycerol-3-phosphocholine.

18:1/16:0-GPC refers to the regioisomer of 16:0/18:1-GPC, 1-oleoyl-2-palmitoyl-sn-glycero-3-phosphocholine.

Nonalcoholic fatty liver disease (NAFLD) refers to a wide spectrum of liver disease including, for example, simple fatty liver (steatosis), nonalcoholic steatohepatitis (NASH), and cirrhosis (irreversible, advanced scarring of the liver). Typically, the stages of NAFLD have in common the accumulation of fat (fatty infiltration) in the liver cells (hepatocytes). In NASH, the fat accumulation is associated with varying degrees of inflammation (hepatitis) and scarring (fibrosis) of the liver. Generally, the genesis of fatty liver is the build-up of excess fat in the liver cells which may lead to inflammation of the liver.

Isolated or purified as used with respect to isolated or purified 1-palmitoyl-2-oleoyl-sn-glycerol-3-phosphocholine (16:0/18:1-GPC), 1-palmitoyl-2-oleoyl-sn-glycerol-3-phosphocholine (16:0/18:1-GPC)-PPARα receptor-ligand complex, or 1-palmitoyl-2-oleoyl-sn-glycerol-3-phosphocholine (16:0/18:1-GPC)-chaperone complex refers to the percentage of 16:0/18:1-GPC, 16:0/18:1-GPC-PPARα receptor-ligand complex, or 16:0/18:1-GPC-chaperone complex present in a composition as compared to the total amount of phosphatidylcholine in the same composition. Thus, an isolated or purified 1-palmitoyl-2-oleoyl-sn-glycerol-3-phosphocholine (16:0/18:1-GPC), 1-palmitoyl-2-oleoyl-sn-glycerol-3-phosphocholine (16:0/18:1-GPC)-PPARα receptor-ligand complex, or 1-palmitoyl-2-oleoyl-sn-glycerol-3-phosphocholine (16:0/18:1-GPC)-chaperone complex indicates that the specified compound constitutes at least about 70% of the total amount of phosphatidylcholine in the composition, preferably about 75%, more preferably about 80%, still more preferably about 85%, even more preferably about 90%, yet more preferably about 95%, still more preferably about 97%, and most preferably about 99% of the total amount of phosphatidylcholine in the composition. In certain instances, the composition may be, for example, a food product.

Wy14,643 refers to 4-Chloro-6-(2,3-xylidino)-2-pyrimidinylthioacetic acid.

Phospholipid refers to a class of lipids and/or fat derivatives in which one fatty acid has been replaced by a phosphate group and one of several nitrogen-containing molecules. Generally, phospholipids contain a diglyceride, a phosphate group, and a simple organic molecule such as choline.

Phosphatidylcholine (PtdCho) refers to a class of phospholipids which incorporate choline as a headgroup.

Phosphocholine (PC) is an intermediate in the synthesis of phosphatidylcholine in tissues.

Chaperone protein refers to a protein, typically a heat shock protein, which generally has among its functions an ability to bind, sequester, repair, and transport other proteins.

WT PPARα-/- null genotype refers to a genetic condition wherein there is an absence of PPARα alleles at any defined loci on homologous chromosomes of the mice genome.

FASKOL PPARα-/- mice genotype refers to a genetic condition in which the alleles of the fatty acid synthase (FAS) gene are absent from the liver tissue of the mice. It may also refer to the absence of PPARα from any defined loci on homologous chromosomes of the mice genome (a genetically null PPARα-/- background).

AdGFP refers to adenoviruses encoding a control protein, green fluorescent protein.

AdFLAG®-PPARα refers to adenoviruses encoding FLAG®-tagged PPARα protein.

AdPPARα refers to an adenovirus encoded PPARα protein.

Ad-ΔDBD-PPARα refers to an adenovirus encoded mutant PPARα protein with a defective DNA Binding Domain (DBD).

AdFLAG$^{-\Delta DBD}$PPARα refers to an adenovirus encoded FLAG®-tagged mutant PPARα protein with a defective DNA Binding Domain (DBD).

DETAILED DESCRIPTION OF THE INVENTION

Surprisingly, it has been discovered that a particular phosphatidylcholine, 1-palmitoyl-2-oleoyl-sn-glycerol-3-phosphocholine (16:0/18:1-GPC), is a physiologically relevant, authentic endogenous PPARα ligand, binding specifically to PPARα. Prior to the presently described discovery, no authentic endogenous PPAR ligand—that is, a molecule occupying the nuclear receptor binding site in vivo while the receptor is actively driving transcription—had been identified.

PPARs are targets for the development of synthetic drugs and the use of the same for the prevention and treatment of disease, and for modulating metabolic and inflammatory pathways by responding to nutritional signals through ligand activation of transcription. Thus, the discovery of an authentic endogenous ligand for PPARα may provide an alternative to synthetic pharmaceuticals for the prevention and treatment of PPARα-dependent (sometimes referred to herein as a PPARα-mediated or PPARα-related) disorders, and in particular, for a PPARα-related liver disorder including, but not limited to, fatty liver disease.

1-palmitoyl-2-oleoyl-sn-glycerol-3-phosphocholine (16:0/18:1-GPC)

16:0/18:1-GPC is a phosphatidylcholine found in various animal organs and tissues, and in particular, for example, in the mammalian brain and liver. 16:0/18:1-GPC generally binds PPARα in the presence of fatty acid synthase (FAS) (i.e., when PPARα is active); however, 16:0/18:1-GPC generally does not bind PPARα in the absence of fatty acid synthase (FAS) (i.e., when PPARα is not active). Competitive inhibition of 16:0/18:1-GPC with a compound that also binds PPARα, such as a pharmacological ligand, typically results in displacement of the 16:0/18:1-GPC in the presence of FAS. Inhibition of the biosynthesis of 16:0/18:1-GPC typically disrupts PPARα-dependent gene expression.

Phosphatidylcholine is ubiquitous in the cell and comprises a substantial proportion of the nuclear volume. It would have a limited capacity to regulate PPARα if high nuclear concentrations ensured constant occupation of the ligand binding site. Liver phosphatidylcholine tends to be highly unsaturated (Lipids 31, 489-495, 1996.), promoting lipoprotein secretion, while lung phosphatidylcholine is saturated (Early Hum Dev 25, 157-171, 1991), facilitating surfactant production. Asymmetric (saturated and unsaturated) fatty acid substituents, symmetric saturated fatty acids, and symmetric unsaturated fatty acids lead to dozens of discrete phosphatidylcholine species. Thus, the forms and concentrations of phosphatidylcholine fatty acids may vary considerably based on, for example, the tissue or organ in which it is located and its functional requirements. By way of example, 16:0/18:1-GPC is present in a number of different organs and tissues in animals, including the human, and may be present in various forms and concentrations, depending on, for example, the activity and functional requirements of the organ, the fatty acid composition of the diet, and/or the physiological demands, such as chronic inflammation or stress, that might lead to remodeling of the fatty acid components of the phospholipid. For example, 16:0/18:1 PC is a minor phosphatidylcholine species in the liver (J Am Soc Mass Spectrom 9, 516-526, 1998), consistent with a role for this species in signaling in that organ. Conversely, for example, 16:0/18:1-GPC is the most abundant phosphatidylcholine species in the brain (Id.), raising the possibility that a different phosphatidylcholine species may activate PPARα in this tissue. This striking diversity could be involved, and, therefore, utilized in tissue-specific PPARα regulation depending on the differential ability of distinct species to recruit co-activators and co-repressors.

Figure 4:
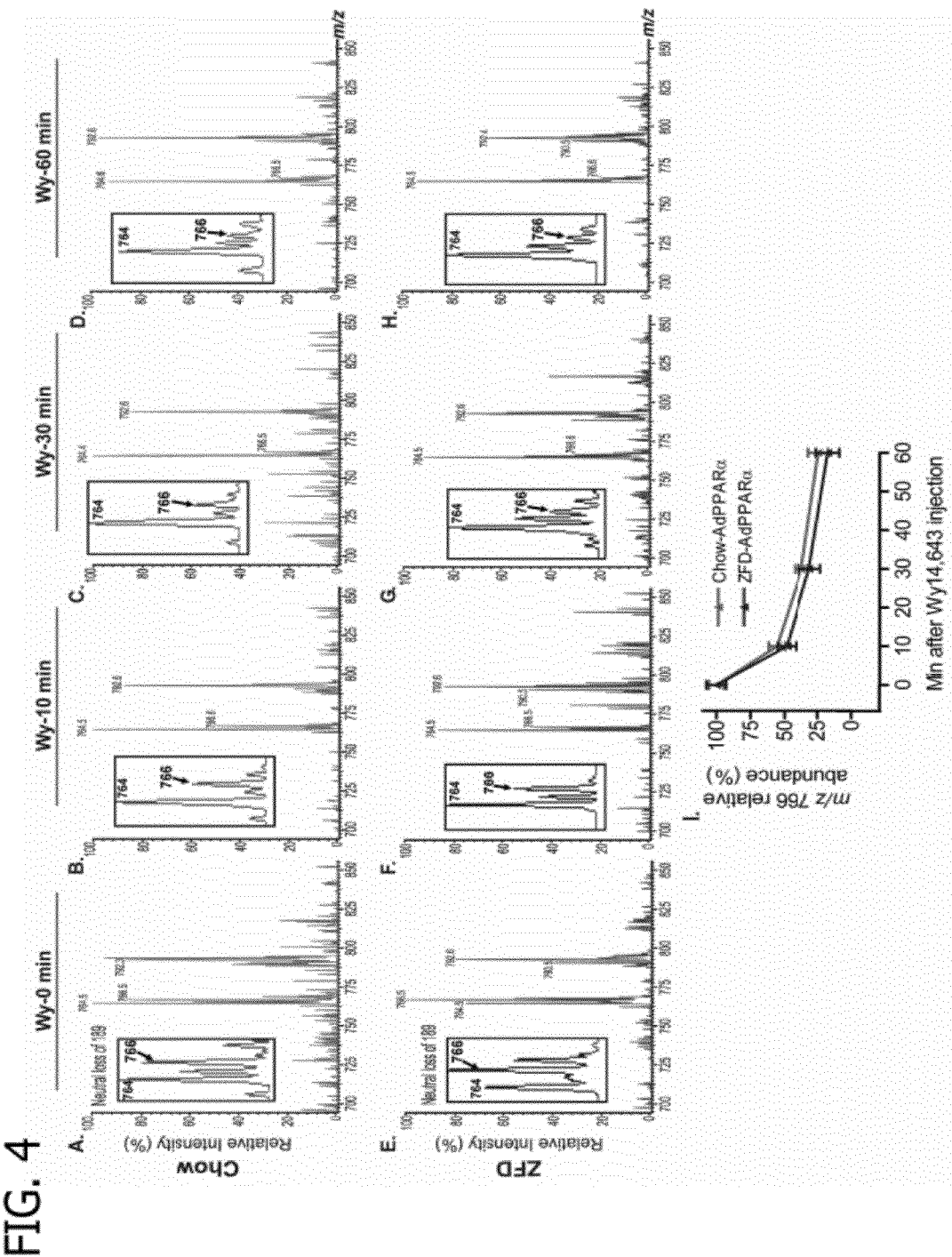
FIG. 4 illustrates electrospray ionization mass spectrometry (ESI/MS) analysis of in vivo competitive inhibition displacement of the endogenous PPARα ligand from PPARα by a PPARα agonist, Wy14,643.
Figure 7:
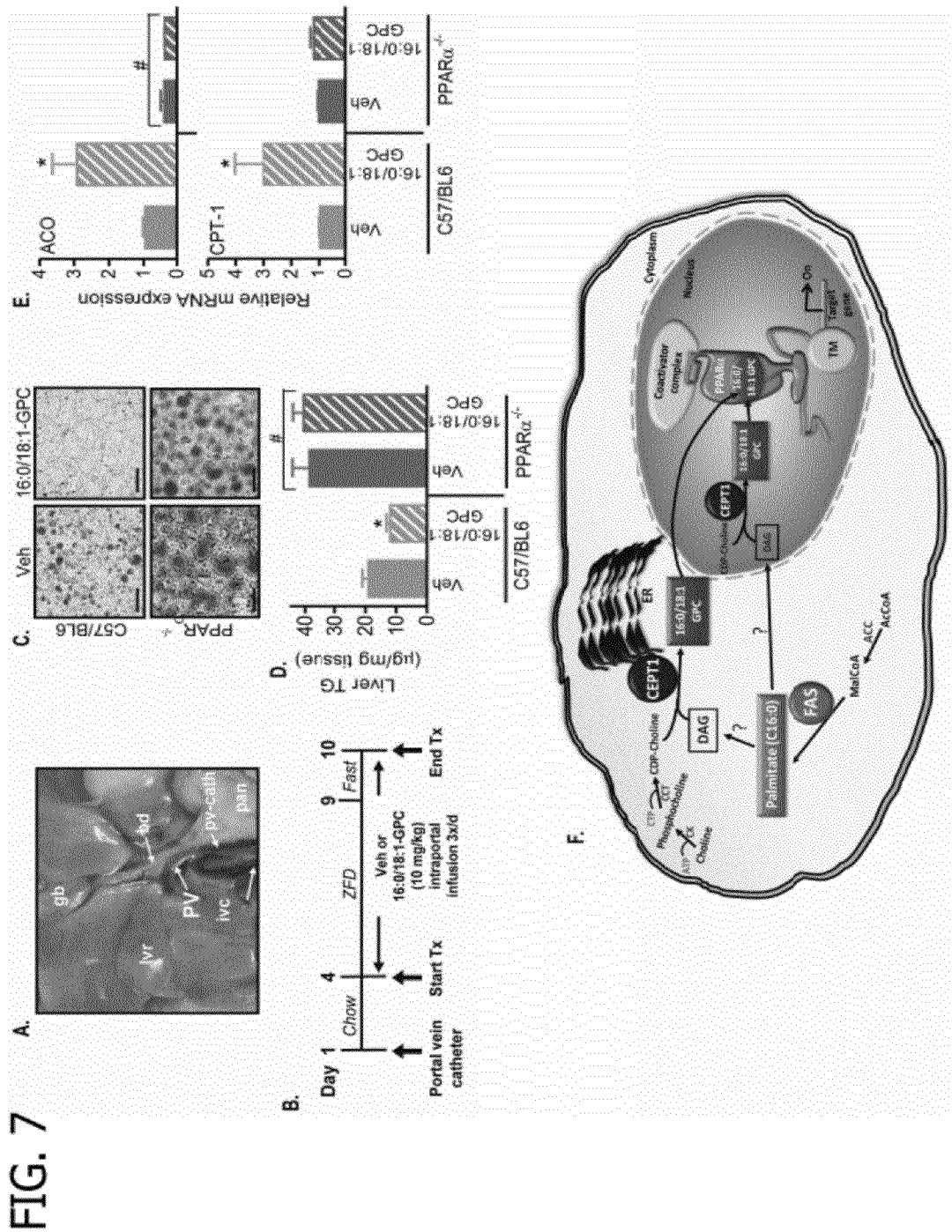
FIG. 7 illustrates portal vein infusion of 1-palmitoyl-2-oleoyl-sn-glycerol-3-phosphocholine (16:0/18:1-GPC) to rescue hepatic steatosis in a PPARα-dependent manner.

16:0/18:1-GPC occupies the PPARα binding site when FAS enzyme activity is present (FIG. 4), as is illustrated, for example, by competitively inhibiting its binding with a known PPARα synthetic ligand, such as, for example, Wy14,643, in cells, tissues, and animals. Without being bound to a single theory, one interpretation of this observation is that FAS, which synthesizes predominantly the saturated fatty acid palmitate (16:0), preferentially channels newly synthesized palmitate through diacylglycerol to the site of phosphatidylcholine synthesis for generation of the PPARα ligand. Previous data also link fatty acid synthesis and phosphatidylcholine synthesis. In cultured cells, sterol regulatory element binding proteins (SREBPs) stimulate the synthesis of phosphatidylcholine (but not other phospholipids), and this effect is attenuated by the FAS-inhibitor cerulenin (Biochem J 372, 811-819, 2003). FIG. 7F illustrates the apparent relationship of fatty acid synthesis, phosphatidylcholine synthesis, and PPARα signaling based on the currently described discoveries.

Systemic levels of free fatty acids change with nutritional status, making PPARα an attractive candidate sensor of energy balance that might respond to fatty acids by accelerating their metabolism. However, this would require that PPARα, a nuclear protein, be exposed to concentrations of fatty acids that reflect those outside the cell. Moreover, a simple diffusion gradient for these lipids in the hepatocyte is unlikely to exist since fatty acids crossing the plasma membrane undergo addition of an acyl-CoA group, leading to a myriad of potential fates including storage in lipid droplets, synthesis of phospholipids, incorporation into intracellular organelles or the external plasma membrane, transport into mitochondria for beta oxidation, association with the ER/Golgi for lipoprotein assembly, and others. This scheme suggests two possibilities: fatty acids are chaperoned from the extracellular environment to the nucleus to activate PPARα, or another entity reflecting nutritional status might be involved in generating the endogenous ligand. Thus, 16:0/18:1-GPC may be combined with a chaperone protein to further enhance, for example, availability, binding efficiency, and efficacy of the 16:0/18:1-GPC for binding PPARα and, therefore, for use in the methods as described below. Such a chaperone would generally be capable of interacting with phospholipids, likely being capable of binding both the charged as well as the uncharged domains. The chaperone would also typically be capable of shuttling between the cytoplasm and the nucleus, both with and without the 16:0/18:1-GPC bound thereto. Because of the potential of the generation of the ligand being related to nutritional status, 16:0/18:1-GPC may be used to affect metabolism or added to food stuffs as also described below.

Both PPARα activation and phosphatidylcholine are thought to be anti-inflammatory. Synthetic PPARα ligands have beneficial effects in animal models of inflammatory disease (Trends Immunol 28, pp. 551-558, 2007). PPARα-deficient mice have enhanced susceptibility to experimental colitis (Lab Invest 84, pp. 1643-1654, 2004) and altered responses in other proinflammatory models. Depletion of PtdCho in liver causes steatohepatitis (Cell Metab 3, pp. 321-331, 2006). PtdCho supplementation decreases symptoms in human ulcerative colitis (Ann Intern Med 147, pp. 603-610, 2007) and suppresses NF-KB activation as well as inflammatory gene expression in cultured cells (J Biol Chem 282, pp. 27155-27164, 2007). Exactly how altering extracellular concentrations of a charged phospholipid species might affect nuclear events is not entirely clear, but there is evidence that certain extracellular phospholipids do not act through a second messenger but instead have direct access to the nuclear receptor PPARα (J Biol Chem 276, pp. 16015-16023, 2001). Therefore, these data are consistent with the discoveries described herein that radiolabelled PtdCho infused into the portal vein leads to preferential accumulation of radioactivity in the nucleus as opposed to the cytoplasm soon after administration (FIG. 12), and that 16:0/18:1 may be useful for formulation an anti-inflammatory compositions.

In addition to affecting lipid metabolism and inflammation, PPARα pathways impact malignancies in complex ways. PPARα agonists cause liver tumors in rodents (Mol Cell Biol 27, pp. 4238-4247, 2007) and PPARα is required for hepatitis C-induced hepatocellular carcinoma in mice (J Clin Invest 118, pp. 683-694, 2008), yet PPARα activation suppresses non-hepatic tumors through effects on angiogenesis (Proc Natl Acad Sci USA 105, pp. 985-990, 2008). Cellular proliferation, a key event in inflammatory pathways, the progression of atherosclerosis, and neoplasia, is associated with changes in nuclear phosphatidylcholine synthesis (J Cell Biol 97, pp. 166-172, 1983; J Biol Chem 276, pp. 8492-8499, 2001). Based on the present findings of a discrete PtdCho serving as the hepatic ligand for PPARα, tissue-specific phospholipid ligands, either induced endogenously or added exogenously, could modify disease processes so that off-target side effects are minimized.

Prevention and Treatment of Disease Using 16:0/18:1-GPC

Administration of 16:0/18:1-GPC to an animal, and in particular, infusion, and more specifically, direct infusion into animal liver cells, altered hepatic lipid metabolism in a PPARα-dependent fashion. Administration of 16:0/18:1-GPC increased the expression of genes controlled by PPARα and known to increase lipid oxidation. Lipid content in the liver was decreased and the resolution of fatty liver achieved. Accordingly, administration of 16:0/18:1-GPC in a therapeutically or prophylactically effective amount to an animal suffering from a PPARα-dependent (sometimes referred to herein as a PPARα-mediated or PPARα-related) disorder can be a treatment for such a disorder, and in particular, for a PPARα-related liver disorder including, but not necessarily limited to, fatty liver disease.

Similarly, administration of either a 16:0/18:1-GPC-PPARα receptor-ligand complex or a 16:0/18:1-GPC-chaperone complex directly to an animal, and in particular, infusion, and more specifically direct infusion into animal liver cells, may also alter hepatic lipid metabolism in a PPARα-dependent fashion, much as did administration of the 16:0/18:1-GPC alone. Accordingly, administration of 16:0/18:1-GPC-PPARα receptor-ligand complex or a 16:0/18:1-GPC-chaperone complex to an animal suffering from a PPARα-dependent disorder can be a treatment for such a disorder, and in particular, for a PPARα-related liver disorder, such as fatty liver disease and other disorders of the liver.

Accordingly, the present invention is directed to methods of prophylaxis and treatment of a PPARα-mediated disorder, and in particular, a PPARα-mediated liver disorder in an animal. It is also directed to a method of prophylaxis or treatment of the particular PPARα-mediated disorder fatty liver disease. It is also directed to methods of lowering triglyceride levels and/or elevating high density lipoprotein levels in an animal suffering from elevated triglyceride levels and/or low high density lipoprotein levels. Related thereto, it is also directed to methods of maintaining lowered (i.e., healthy) triglyceride levels and/or elevated (i.e., healthy) high density lipoprotein (HDL) levels in an animal. The methods generally comprise administering a prophylactic or therapeutic amount of 1-palmitoyl-2-oleoyl-sn-glycerol-3-phosphocholine (16:0/18:1-GPC), a 1-palmitoyl-2-oleoyl-sn-glycerol-3-phosphocholine-chaperone (16:0/18:1-GPC-chaperone), a 1-palmitoyl-2-oleoyl-sn-glycerol-3-phosphocholine-chaperone complex (16:0/18:1-GPC-chaperone complex), a 16:0/18:1-GPC-PPARα receptor-ligand complex, or a combination thereof described above to a patient. The method typically lowers triglyceride levels, for example, from a fasting level (generally understood to be 12 hours of fasting prior to drawing of the blood used for testing) of about 150 mg/dl (mg of triglyceride/dl of blood) or greater, a range that is considered to be abnormal by the National Cholesterol Education Program, to a triglyceride level within an acceptable range (sometimes referred to herein as healthy level or range) of a fasting level of less than about 150 mg/dl, a range that is considered to be normal by the National Cholesterol Education Program. The method may also be utilized to maintain such an acceptable level/range. Similarly, the method typically elevates HDL levels, for example, from a fasting level of about 40 mg/dl or less, a range that is considered to be abnormal by the National Cholesterol Education Program, to a HDL level within an acceptable range (sometimes referred to herein as healthy level or range) of a fasting level of more than about 40 mg/dl, and preferably a fasting level of more than about 60 mg/dl, a range that is considered to be normal by the National Cholesterol Education Program. The method may also be utilized to maintain such an acceptable level/range.

Patients suitable for the treatment described herein include patients presenting with or suffering from the symptoms of a PPARα-related disorder. Typically, such patients will present with signs such as, for example, those related to the presence of elevated triglyceride levels, decreased high density lipoprotein levels, and evidence of insulin resistance, which may include, for example, elevated glucose levels and elevated blood pressure. Typically, such symptoms will include, for example, fatigue, weight gain, and eventually heart attack. Suitable patients also include those at risk for developing a PPARα-related disorder. Suitable patients include any animal, and in particular any mammal, having or at risk for the development of a PPARα-related disorder or the presentation of the described symptoms, including, for example, human, canine, feline, equine, bovine, and porcine patients.

Prophylaxis or treatment may include administration of a prophylactic or therapeutically effective amount of the compositions of the present invention in a form described herein to a subject in need of treatment. The compositions of the present invention can be administered in any well known manner that results in a decrease or complete loss of symptomatology associated with a PPARα-mediated disorder. Suitable manners of administering the compositions of the present invention include, for example, oral administration; parenteral administration, including, for example, intravenous, intraarterial, subcutaneous, intramuscular, intraorbital, intracapsular, intraspinal, intraperitoneal, or intrasternal administration. The compositions may be administered in any conventional manner available for use in conjunction with pharmaceuticals, either as individual prophylactic or therapeutic agents or in a combination of prophylactics or therapeutics.

As with the selection of dosages, the preferred route of administration will vary with a number of factors, such as, for example, the disorder being treated and the severity of the disorder; activity of the specific compound employed; the specific composition employed; the age, body weight, general health, sex and diet of the patient; the time of administration; the rate of excretion of the specific compound employed; the duration of the treatment; drugs used in combination or coincidental with the specific compound employed and like factors well known in the medical arts. For example, it is well within the skill of the art to administer doses in a particular manner initially, for example, to cause a rapid increase or "loading" of the compound or composition in the patient prior to the administration of the compound in an alternative or different manner, for example, to maintain a particular level or concentration of the compound or composition in the blood or tissues of the patient.

Regardless of the mode of administration, generally targeted administration of the compositions disclosed herein may not be necessary, particularly as disclosed in the examples. Accordingly, systemic administration as disclosed above is contemplated. Alternatively, the compositions disclosed herein may be targeted to a particular organ, such as, for example, the liver, the brain, the heart, coronary arteries, carotid arteries, the kidney, endothelial cells, skeletal muscle, and/or lungs by methods known to those skilled in the art.

Accordingly, in one embodiment of the method of treating a PPARα-related disorder in a mammal, the method comprises administering a therapeutically effective amount of 1-palmitoyl-2-oleoyl-sn-glycerol-3-phosphocholine (16:0/18:1-GPC) to said mammal. The 16:0/18:1-GPC may be an isolated form of the compound.

As mentioned above, the 16:0/18:1-GPC may also be administered as a complex with a chaperone. A chaperone is a protein that generally has the ability to bind, sequester, repair, and/or transport another compound, such as another protein. Fatty acids crossing the plasma membrane undergo addition of an acyl-CoA group, leading to a myriad of potential fates including storage in lipid droplets, synthesis of phospholipids, incorporation into intracellular organelles or the external plasma membrane, transport into mitochondria for beta oxidation, association with the endoplasmic reticulum/Golgi for lipoprotein assembly, and others. Without being bound to a single theory, this scheme suggests that fatty acids are chaperoned from the extracellular environment to the nucleus to activate PPARα or that another entity reflecting nutritional status might be involved in generating the endogenous ligand. For example, 16:0/18:1-GPC may be chaperoned from the extracellular environment of a cell to the nucleus of the same cell to activate PPARα. Examples of possible chaperones that may be utilized as part of a 16:0/18:1-GPC-chaperone complex include, for example, FABP1 and FABP4 (fatty acid binding protein 1 and fatty acid binding protein 4, respectively).

In addition to methods utilizing the administration of 16:0/18:1-GPC, another embodiment of the present invention includes methods of treatment comprising, either in combination with administration of a composition comprising 16:0/18:1-GPC or in lieu of the same, administration of a 16:0/18:1-GPC-receptor-ligand complex, and in particular administration of a 16:0/18:1-GPC-PPARα complex. Applicants isolated a receptor-ligand complex which comprises 16:0/18:1-GPC bound to PPARα.

Similarly, the compositions of the present invention, including compositions comprising one or more of 16:0/18:1-GPC, 16:0/18:1-GPC-receptor-ligand complex, 16:0/18:1-GPC-chaperone complex, a 16:0/18:1 chaperone, or a combination thereof, may be administered to a patient to restore and/or activate the expression of hepatic acyl-CoA oxidase (ACO or AOX) and carnitine palmitoyl transferase I (CPT-1) in a PPARα-dependent manner. Routes of administration and dosages for these compositions are as described below.

Formulations of the Compositions for Administration to Patients

The compositions described herein are suitable for use in the prophylaxis or treatment of PPARα-mediated disorders, and in particular liver disorders caused by or associated with PPARα, such as, for example, fatty liver disease. The compositions, therefore, can be prepared as formulations for administration to animals, more specifically mammals, and in particular humans. These compositions may comprise an isolated or pure, or substantially isolated or pure, form of 16:0/18:1-GPC that can be readily administered by any means disclosed herein, such as for example, by oral administration or by injection.

Similarly, the compositions may also comprise additional components that are typically used to formulate compositions suitable for administration to mammals. The addition of such components will depend in large part upon the mode of administration. The route of administration, and in particular the preferred route of administration, may depend on factors such as, for example, the disorder being treated and the severity of the disorder; activity of the specific compound employed; the specific composition employed; the age, body weight, general health, sex and diet of the patient; the time of administration; the rate of excretion of the specific compound employed; the duration of the treatment; drugs used in combination or coincidental with the specific compound employed and like factors well known in the medical arts. In any event, the composition may additionally comprise a "pharmaceutical carrier" such as a pharmaceutically acceptable buffer, suspending agent, or vehicle for delivering the composition of the present invention to the mammal or human. The carrier may be liquid or solid, although it is preferably a liquid, and is selected consistent with the manner of administration. A "pharmaceutically acceptable" component is one that is suitable for use with humans and/or animals without undue adverse side effects (such as toxicity, irritation, and allergic response) commensurate with a reasonable benefit/risk ratio. Such components may be easily determined by those skilled in the art.

For oral administration, the compounds can be formulated readily by combining the active compound with pharmaceutically acceptable excipients well known in the art. Such excipients enable the compounds of the invention to be formulated as tablets, pills, dragees, capsules, liquids, gels, syrups, slurries, suspensions, wafers, and the like, for oral ingestion by a patient to be treated. Pharmaceutical preparations for oral use can be prepared having a liquid active, such as an oil or water based active ingredient that is encapsulated in an excipient, filler, or carrier to form, for example, a gel-cap or other semi-solid capsule form of the composition capable of being administered orally. Suitable excipients include, for example, fillers such as sugars, including lactose, sucrose, mannitol, or sorbitol, cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP). If desired, disintegrating agents may be added, such as the cross-linked polyvinyl pyrrolidone, agar, or alginic acid or a salt thereof such as sodium alginate.

Formulations suitable for parenteral administration include aqueous and non-aqueous sterile formulations isotonic with the blood of the intended recipient; and aqueous and non-aqueous sterile suspensions which may include suspending systems designed to target the compound to blood components or one or more organs, and in particular, to the liver. The formulations may be presented in unit-dose or multi-dose sealed containers, for example, ampoules or vials. Injections, solutions and suspensions may be prepared from sterile powders, granules and tablets as known to those skilled in the art. Parenteral and intravenous forms may also include minerals or other materials to make them compatible with the type of injection or delivery system chosen.

In general, water, suitable oil, saline, aqueous dextrose (glucose), or related sugar solutions and glycols such as propylene glycol or polyethylene glycols are suitable carriers for parenteral solutions. Solutions for parenteral administration preferably contain a water soluble salt of the active ingredient, a carrier, and optionally stabilizing agents, buffers, or preservatives. Sodium bisulfite, sodium sulfite, ascorbic acid, citric acid or salts thereof, and EDTA or salts thereof are suitable stabilizing agents. Preservatives include, for example, benzalkonium chloride, methyl- or propyl-paraben, or chlorobutanol.

The present invention additionally contemplates administering compounds as described for use in the form of veterinary formulations, which may be prepared, for example, by methods that are conventional in the art in light of the present disclosure.

Accordingly, the present invention is also directed to a composition for the prophylaxis or treatment of a PPARα-related disorder in an animal, the composition comprising a prophylactically or therapeutically effective amount of 16:0/18:1-GPC, a 16:0/18:1-GPC-receptor-ligand complex, and in particular a 16:0/18:1-GPC-PPARα complex, a 16:0/18:1-GPC-chaperone, a 16:0/18:1-GPC-chaperone complex, and/or any combination thereof. In one embodiment, the composition is in a formulation as outlined above, and in a particular embodiment, comprises a pharmaceutically acceptable carrier.

Dosages of the Present Compositions

Any suitable dosage may be administered in the methods of the present invention. The form of the composition chosen for a particular application, the carrier, and the amount will vary widely depending on the species of the warm blooded animal or human, the disease or state thereof being treated, and the effective concentrations observed in trial studies.

The specific prophylactically or therapeutically effective dose level for any particular patient will depend upon a variety of factors including the disorder being treated and the severity of the disorder; activity of the specific compound employed; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of the compound at levels lower than those required to achieve the desired prophylactic or therapeutic effect and to gradually increase the dosage until the desired effect is achieved. If desired, the effective daily, weekly, or monthly dose may be divided into multiple doses for purposes of administration. Consequently, single dose compositions may contain such amounts or submultiples thereof to make up the daily, weekly, monthly, yearly or other dose.

Generally, a dose of least about 5 mg per kilogram of body weight, and preferably a dose of at least about 10 mg per kilogram of body weight, is administered to a patient depending on the factors mentioned above. Preferably, the dosage range may be between about 5 mg and about 50 mg per kg of body weight, more preferably about 10 mg to about 45 mg per kilogram of body weight, even preferably about 10 mg to about 40 mg per kilogram of body weight, still more preferably about 10 mg to about 35 mg per kilogram of body weight, and yet more preferably about 10 mg to about 30 mg per kilogram of body weight. In one embodiment, the dose is about 5 mg per kilogram of body weight, preferably about 10 mg per kilogram of body weight, more preferably about 15 mg per kilogram of body weight, even more preferably about 20 mg per kilogram of body weight, still more preferably about 25 mg per kilogram of body weight, and most preferably about 30 mg per kilogram of body weight. Generally, these doses may be administered on a per day basis.

The requisite dosage may be administered as a single administration of the compound or complex or multiple administrations of the compound or complex. Multiple administrations may be provided over the course of a single day, multiple days, weeks, or months. In some embodiments, multiple administrations are provided over the course of one to seven consecutive days. In some embodiments, three to seven administrations are provided over the course of three to seven days, and in particular consecutive days. In some embodiments, five administrations are provided over the course of five days, and in particular consecutive days.

In one embodiment, a single administration of between about 5 mg and about 50 mg per kilogram of body weight is administered. In another embodiment, a single administration of between about 10 mg and about 45 mg per kilogram of body weight is administered. In another embodiment, a single administration of between about 10 mg and about 40 mg per kilogram of body weight is administered. In another embodiment, a single administration of between about 10 mg and about 35 mg per kilogram of body weight is administered. In another embodiment, a single administration of between about 10 mg and about 30 mg per kilogram of body weight is administered. In another embodiment, a single administration of about 5 mg per kilogram of body weight, preferably about 10 mg per kilogram of body weight, more preferably about 15 mg per kilogram of body weight, even more preferably about 20 mg per kilogram of body weight, still more preferably about 25 mg per kilogram of body weight, and most preferably about 30 mg per kilogram of body weight is administered.

Generally the composition of the present invention may be administered on a daily, weekly, monthly or on an as needed basis, either in a single administration or separate administrations comprising one or more doses of the composition. Accordingly, in one embodiment, multiple administrations of about 5 mg to about 50 mg per kilogram of body weight are provided. In another embodiment, multiple administrations of about 10 mg to about 30 mg per kilogram of body weight are provided. In another embodiment, multiple administrations of about 5 mg to about 50 mg per kilogram of body weight are provided over the course of one to seven days, and preferably consecutive days. In another embodiment, multiple administrations of about 10 mg to about 30 mg per kilogram of body weight are provided over the course of one to seven days, and preferably consecutive days. In another embodiment, multiple administrations of about 5 mg per kilogram of body weight, preferably about 10 mg per kilogram of body weight, more preferably about 15 mg per kilogram of body weight, even more preferably about 20 mg per kilogram of body weight, still more preferably about 25 mg per kilogram of body weight, and most preferably about 30 mg per kilogram of body weight are provided over the course of one to seven days, and preferably consecutive days.

The dosage and the dosage regimen will vary depending on the ability of the patient to sustain the desired effective results. The dosing regimen, therefore, may be a single dose administered once, once a day, once a week, once a month, biannually, annually, or even less frequently for the duration of the presentation of the patient's symptoms, for a period exceeding the same, or for the patient's lifetime either to treat or prevent the recurrence of symptomatology. Likewise, the dosing regimen may be multiple doses administered over the course of a single day, days, weeks, months, or years for the duration of the presentation of the patient's symptoms, for a period exceeding the same, or for the patient's lifetime either to treat or prevent the recurrence of symptomatology.

Methods of Diagnosis of PPARα-Mediated Disorders

Another embodiment of the present invention utilizes the discovery of 16:0/18:1-GPC as the endogenous ligand of PPARα to diagnose the presence or absence of a PPARα-mediated disorder in a patient. Typically, a sample from a patient, such as, for example, a blood, a cell, or a tissue sample, including cell samples taken from tissue culture preparations or cells isolated by any process from a tissue or biopsy sample, is obtained. In one embodiment, the sample is liver cells or liver tissue. Once obtained, the sample is treated such that the compound or complex of interest, generally 1-palmitoyl-2-oleoyl-sn-glycerol-3-phosphocholine (16:0/18:1-GPC), a 16:0/18:1-GPC-PPARα receptor-ligand complex, a chaperone of 16:0/18:1-GPC, and/or a 16:0/18:1-GPC-chaperone complex, can be isolated and the concentration or amount of one or more of the compounds or complexes may be measured or determined and compared, if necessary, to one another. The concentration of one or more of these compounds or complexes, including a comparison of the concentrations or amounts of one or more of the compounds or complexes to one another, is then utilized to determine the presence or absence of a PPARα-mediated disorder. Manners of detecting and measuring the amounts of the compound or complex of interest is easily accomplished according to methods known in the art, including, for example, immunoprecipitation, immunoblotting, mass spectrometry, and RT-PCR of, for example, PPARα-dependent genes such as acyl-CoA oxidase (ACO) and carnitine palmitoyl transferase I (CPT-I) as illustrated, for example, in FIGS. 1-7.

Accordingly, another embodiment of the present invention is a method of determining the presence or absence of a PPARα-related disorder, and in particular, a liver disorder, in a patient. The method comprises lysing liver cells obtained from the patient to form lysed cells; isolating a PPARα-1-palmitoyl-2-oleoyl-sn-glycerol-3-phosphocholine (16:0/18:1-GPC) receptor-ligand complex from the lysed cells; measuring the amount of the PPARα-1-palmitoyl-2-oleoyl-sn-glycerol-3-phosphocholine (16:0/18:1-GPC) receptor-ligand complex; and determining the presence or absence of a PPARα-related liver disorder based on the amount of the complex. In a particular embodiment, the patient is a mammal, preferably a human, a canine, a feline, or an equine, and most preferably a human.

Another embodiment of the present invention is a method of determining the presence or absence of a PPARα-related disorder, and in particular a liver disorder, in a patient possibly suffering from such a disorder. The method comprises lysing liver cells obtained from a patient to form lysed cells; isolating a chaperone, 1-palmitoyl-2-oleoyl-sn-glycerol-3-phosphocholine (16:0/18:1-GPC), and a 1-palmitoyl-2-oleoyl-sn-glycerol-3-phosphocholine (16:0/18:1-GPC)-chaperone complex from the lysed cells; measuring the amount of the chaperone, the 1-palmitoyl-2-oleoyl-sn-glycerol-3-phosphocholine (16:0/18:1-GPC), and the 1-palmitoyl-2-oleoyl-sn-glycerol-3-phosphocholine (16:0/18:1-GPC)-chaperone complex; and determining the presence or absence of a PPARα-related liver disorder based on the amounts of the chaperone, the 1-palmitoyl-2-oleoyl-sn-glycerol-3-phosphocholine (16:0/18:1-GPC), and the 1-palmitoyl-2-oleoyl-sn-glycerol-3-phosphocholine (16:0/18:1-GPC)-chaperone complex. In a particular embodiment, the patient is a mammal, preferably a human, a canine, a feline, or an equine, and most preferably a human.

Generation of Transgenic Mice

Another aspect of the present invention is the creation of transgenic animals, and in particular transgenic mice, useful for the detection and testing of the effects of 16:0/18:1-GPC on PPARα-related disorders. In order to properly characterize and identify the endogenous PPARα ligand, several factors had to be controlled within the test mice. Thus, mice had to be created that were FAS-inactivated (to determine the effects of the presence and absence of FAS on PPARα-induced gene expression), that were PPARα null (as a control to determine the binding capacity and effects of the deduced endogenous ligand), and/or some combination thereof.

Thus, another embodiment of the present invention is a transgenic FASKOL mouse that is also PPARα$^{-/-}$. These mice are created by genetically crossing FASKOL mice with PPARα null mice. FASKOL mice were generated as described in Cell Metab 1, pp. 309-322, 2005, while the PPARα mice (originally generated by the laboratory of Frank Gonzalez at NIH) were obtained from the Jackson Laboratories (Bar Harbor Me.). Generally, FASKOL mice exhibit impaired PPARα-dependent gene expression, which may be subsequently rescued after pharmacological activation of PPARα (Cell Metab 1, pp. 309-322, 2005), thereby suggesting a role of FAS. As the experiments discussed below utilized andenovirally transduced PPARα in the mice, it was necessary to be able to create a FASKOL mouse in a PPARα$^{-/-}$ background to be able to eliminate the possibility of ligand competition between the andenovirally transduced PPARα and the endogenous PPARα.

Results of experiments utilizing these mice may be found in the Examples below.

Food Products with Altered 16:0/18:1-GPC Content and the Use of the Same to Improve Metabolism Systemic levels of free fatty acids change with nutritional status, making PPARα an attractive candidate sensor of energy balance that might respond to fatty acids by accelerating their metabolism. There is evidence that a nutritionally responsive entity may generate the endogenous PPARα ligand. Fatty acid synthase (FAS) catalyzes the first committed step in fatty acid biosynthesis, utilizing acetyl-CoA, malonyl-CoA and NADPH to generate mostly the saturated fatty acid palmitate (Prog Lipid Res 36, pp. 43-53, 1997). Liver-specific inactivation of FAS results in mice with decreased PPARα-dependent gene expression and a phenotype resembling PPARα deficiency (Cell Metab 1, 309-322, 2005). This suggests that FAS, which synthesizes palmitate 16:0, is involved in generation of the PPARα cellular ligand. The phenotype is reversed and gene expression rescued after pharmacologic activation of PPARα. This phenomenon is not limited to the liver. Selective inactivation of FAS in the hypothalamus impairs PPARα-dependent gene expression and alters feeding behavior (J Clin Invest 117, 2539-2552, 2007). Both are corrected after hypothalamic infusion of a PPARα activator. It thus appears that FAS, known to be regulated by nutrition, is required in some tissues to generate the endogenous ligand for PPARα.

Thus, it has been discovered that consumption of foods modified with 1-palmitoyl-2-oleoyl-sn-glycerol-3-phosphocholine as part of a dietary regimen improves the metabolism of a mammalian subject. The foods may be modified in any number of well known ways, as long as the ultimate result is a food product having increased (sometimes referred to as supplemental) amounts or concentrations of 16:0/18:1-GPC relative to the same food product in its unmodified (or non-supplemented) form. This can be achieved, for example, by adding 16:0/18:1-GPC to the food products. Glycerophospholipids are currently of commercial importance and considered beneficial to the human health. (*Biotechnology Advances* 23, pp. 203-259, 2005). Commercially available phosholipids are soybean lecithin, with a typical composition of PC, 20%; PE, 15%, PI, 20%; PA and other phosphatides, 5%; carbohydrates and sterols, 5%; and glycerides, 35% (J Am Oil Chem Soc 1976; 53:425-427). Eggs, organ meats, fishes, soya, and oilseeds are rich sources of PLs, especially for PC, whereas leafy vegetables, fruits, and roots are, with few exceptions, relatively poor sources of PLs. (*Biotechnology Advances* 23, pp. 203-259, 2005). Meats and tissues from different sources but performing similar functions have similar relative PL distribution. Id. On the other hand, they can be markedly influenced by the factors such as breed, age, sex, season, and feeding habits (J Am Oil Chem Soc 1983; 60(12): 1971-1978).

Accordingly, another embodiment of the present invention is a method for modifying the 1-palmitoyl-2-oleoyl-sn-glycerol-3-phosphocholine (16:0/18:1-GPC) content of food, said method comprising adding 1-palmitoyl-2-oleoyl-sn-glycerol-3-phosphocholine (16:0/18:1-GPC) to a food product. Another aspect of the present invention related thereto is a modified food product having increased or supplemental 16:0/18:1-GPC amounts or concentrations, said food product being obtained according to said method. Exemplary food products include milk and milk products, and in particular milk shakes, soybeans and soybean products, eggs and egg products, and whole grain products, as well as other products in which phospholipids are generally found, and more specifically, generally found in high concentrations.

Also related thereto is a method for improving the metabolism of a mammal utilizing the modified food products described above. This method generally comprises administering to said mammal a modified food product comprising an increased amount of or supplemental 1-palmitoyl-2-oleoyl-sn-glycerol-3-phosphocholine (16:0/18:1-GPC).

Having described the invention in detail, it will be apparent that modifications and variations are possible without departing from the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Where appropriate in the examples throughout this application, comparisons were performed using an unpaired, two-tailed Student's t-test or analysis of variance (ANOVA). If the overall F was significant for the latter, comparisons between means were made using appropriate post hoc tests.

Example 1

The primary objective was to identify and characterize an endogenous PPARα ligand and to test the hypothesis that de novo lipid biosynthesis generates the physiologically relevant endogenous ligand 1-palmitoyl-2-oleoyl-sn-glycerol-3-phosphocholine (16:0/18:1-GPC) for PPARα. A strategy based on purifying a tagged PPARα molecule from the livers of mice with or without expression of fatty acid synthase (FAS) was developed (see FIG. 1). Fatty acid synthase knock-out in liver (FASKOL) mice which manifest impaired PPARα-dependent gene expression that is rescued after pharmacological activation of PPARα (Cell Metab 1, pp. 309-322, 2005) were crossed with PPARα null mice to generate liver-specific FAS knockout mice on a PPARα null background, to reconstitute liver PPARα expression, and to eliminate the possibility of ligand competition between adenovirally transduced PPARα and endogenous PPARα (see FIG. 1).

Animals and Reagents

Animal protocols were approved by the Washington University Animal Studies Committee. Mice were genotyped using previously described primer sets (Nat Med 9, pp. 1069-1075, 2003; Cell Metab 1, pp. 309-322, 2005) and fed either chow (Purina 5053) or a zero-fat diet (ZFD) (Harlan Teklad, TD03314). Experiments were performed at 16-20 wks of age to allow for maximal effects of albumin-Cre. Assays were performed as described (Cell Metab 1, pp. 309-322, 2005). 1-Palmitoyl-2-Oleoyl-sn-Glycero-3-Phosphocholine (PC16: 0/18:1) and its regioisomer, 1-Oleoyl-2-Palmitoyl-sn-Glycero-3-Phosphocholine (PC18:1/16:0) were obtained from Avanti Polar Lipids (Alabaster, Ala.). STEALTH™ siRNA oligonucleotides for mouse ChPT1 (GGAGGAGCAACAAUGUGGGACUAUA) (SEQ ID NO: 1) and CEPT1 (UGGCAGUGAUUGGAGGACCACCUUU) (SEQ ID NO: 2) were from Invitrogen (Carlsbad, Calif.).

Adenoviruses

Adenovirus encoding both FLAG®-tagged wild type mouse PPARα and a GFP marker, and an adenovirus encoding GFP alone were gifts from T. C. Leone and D. P. Kelly. The AdPPARα virus is known to result in expression of a protein that transactivates PPARα target genes (Bernal-Mizrachi et al., 2003; Tordjman et al., 2002). The DNA binding domain (DBD) mutant of PPARα was generated by mutating the two highly conserved cysteine residues (Shi et al., 2002) to alanine (C119A, C122A) using site-directed mutagenesis (QuikChange® kit, Stratagene). The DBD mutant was subcloned into the pCMV-TAG1 vector (Stratagene) to acquire a FLAG® tag, then shuttled into pAdTrack-CMV vector encoding a GFP marker and recombined with Ad-Easy1 vector. The pAdTrack-CMV and pAdEasy-1 vectors were gifts from the laboratory of B. Vogelstein. Viruses were purified and expanded as described (Bernal-Mizrachi et al., 2003; Tordjman et al., 2002). The presence of GFP in each of the adenoviruses allowed a simple estimation of transduction efficiency. Viruses were administered by slow intravenous infusion at a dose of $8.5 \times 10^{10}$ PFU, each in a total volume of 200 µl. Livers were rapidly removed on day 4 after injections, a time period noted to produce optimal viral transduction (Bernal-Mizrachi et al., 2003) and FLAG®-tagged PPARα was isolated.

Histology

Livers were frozen in Tissue-Tek OCT and 5-10 µm sections were cut using a cryostat. Sections were placed on glass slides and subjected to immunofluorescence microscopy for GFP, or stained with oil red O (Sigma-Aldrich Co., St. Louis) to detect neutral lipids. Images were captured though a NIKON® Eclipse E600 microscope attached to a Photometrics CoolSNAP™ digital camera.

Isolation of Tagged PPARα

Freshly harvested livers (~100 mg) were gently homogenized in ice-cold non-detergent hypotonic buffer (10 mM HEPES, pH 7.9, 1.5 mM $MgCl_2$, 10 mM KCl, 100 mM DTT, protease and phosphatase inhibitor cocktail). After an additional 10 min incubation in the hypotonic buffer, the homogenate was centrifuged at 8000×g at 4° C. for 20 min. The pellet was homogenized in ice-cold extraction buffer (10 mM HEPES, pH 7.9, 1.5 mM $MgCl_2$, 0.21 M NaCl, 0.2 mM EDTA, 25% (v/v) glycerol, 100 mM DTT, protease and phosphatase inhibitor cocktail), placed on a rotating shaker at 4° C. for 1 h, then centrifuged at 18,000×g for 10 min. The supernatant (nuclear fraction) was incubated with anti-FLAG® M2-Agarose affinity gel (A2220, Sigma-Aldrich, St. Louis) overnight at 4° C. on a rotating shaker. Four washes (50 mM Tris HCl, pH 7.4, 100 mM NaCl, protease and phosphatase inhibitor cocktail), were followed by elution using competition with excess 3× FLAG® peptide (F4799, Sigma-Aldrich, St. Louis; 150 ng/µl). An aliquot of the complex was processed for immunoblotting; the remainder was transferred to methanol/chloroform and processed for mass-spectrometry. These processes are well known (see, e.g., J Am Soc Mass Spectrom 14, pp. 352-363, 2003; J Mass Spectrom 38, pp. 752-763, 2003; Analytical Biochemistry, 155(1), pp. 71-77, (1986)).

Strategy for Detecting the Endogenous PPARα Ligand

FIG. 1E depicts a strategy for detecting the endogenous PPARα ligand. Mice were infected with an adenovirus directing expression of a FLAG®-tagged PPARα. This was followed by affinity-based (utilizing an antibody recognizing the FLAG® epitope) biochemical isolation of PPARα under conditions (such as the absence of detergent) unlikely to disrupt the ligand/nuclear factor interaction and which yielded a dominant PPARα band on protein-stained gels (not shown). Affinity matrix eluates were subjected to lipid analysis via mass spectrometry analysis to determine the identity of the endogenous ligand bound to the PPARα. Lipid analyses of the affinity matrix eluates revealed only one peak that was FAS-dependent and this was found in a portion of the phospholipid spectra. A peak with mass to charge ratio (m/z) of 766.5 bound to PPARα purified from livers expressing FAS (arrow, FIG. 2B) and its abundance was significantly decreased in PPARα purified from FAS-deficient livers (arrow, FIG. 2D). The abundance of m/z 766.5 increased in PPARα purified from WT mice fed a diet high in carbohydrates (ZFD) (arrow, FIG. 2F, compare m/z 766 to m/z 764 in FIGS. 2F and 2B) but remained decreased with FAS deficiency (arrow, FIG. 2H). Quantitation of peak abundance for independent experiments is presented in FIG. 2I. Increased association of m/z 766 with PPARα after high carbohydrate feeding and its decreased detection with FAS deficiency indicates that this phospholipid is FAS-related.

Confirmation of the Absence of Endogenous PPARα

Affinity matrix eluates were further subjected to immunoprecipitation followed by immunoblotting. These processes are well known; see e.g. Analytical Biochemistry, 155(1), pp. 71-77, 1986. In general, it is common to carry out immunoblotting after subjecting samples to SDS-PAGE. Cell and tissue lysates were prepared by homogenization in a modified RIPA buffer containing a cocktail of protease and phosphatase inhibitors (Chakravarthy et al., 2005). 25 µg of total protein or an aliquot of the FLAG®-eluted protein/lipid mixture was resolved by SDS/PAGE (10% polyacrylamide). Gels were stained with GelCode Blue Protein stain (Thermo Scientific, Waltham, Mass.), a highly sensitive Coomassie G-250-based protein stain, for 1 h followed by destaining in ultrapure water for 4 h. Other gels were transferred onto PVDF membranes (Millipore Corp., Billerica Mass.), and blotted using the following antibodies: FAS (1:1000, Abcam, Cambridge, Mass.), FLAG® M2 monoclonal antibody (1:2000, Sigma-Aldrich Co., St. Louis), PPARα (1:750, Santa Cruz Biotechnology, Santa Cruz, Calif.), actin (1:5000, Sigma-Aldrich Co., St. Louis, Mo.), and PCNA (1:1000, Cell Signaling Technology, Danvers, Mass.), followed by appropriate secondary antibody incubation at 1:5000-1:7500 dilution, and detection by chemiluminescence (ECL kit, Amersham, Piscataway, N.J.). Except as otherwise noted herein, therefore, the process of the present invention is carried out in accordance with such processes. The results confirm the absence of endogenous PPARα (FIG. 1F, lanes 1 and 3) and indicate that the yield of tagged PPARα from liver was similar in mice with and without expression of FAS (FIG. 1F, lanes 2 and 4).

Strategy to Determine the Non-Specificity of Lipid Binding to GFP

Affinity matrix eluates (with equal protein content) of nuclear fractions from mice infected with AdGFP (as a control) or AdPPARα in the presence (WT/PPARα–/–) or absence (FASKOL/PPARα–/–) of FAS were subjected to a lipid extraction followed by mass spectrometric analysis of phospholipids, fatty acids, and triglycerides. No appreciable lipid signal was detected from GFP eluates (see FIGS. 2A, 2C, 2E and 2G) for a portion of the phopholipid spectra; triglyceride and fatty acid signals were also essentially absent (data not shown), suggesting that nonspecific binding of lipids to GFP protein was minimal.

Figure 8:
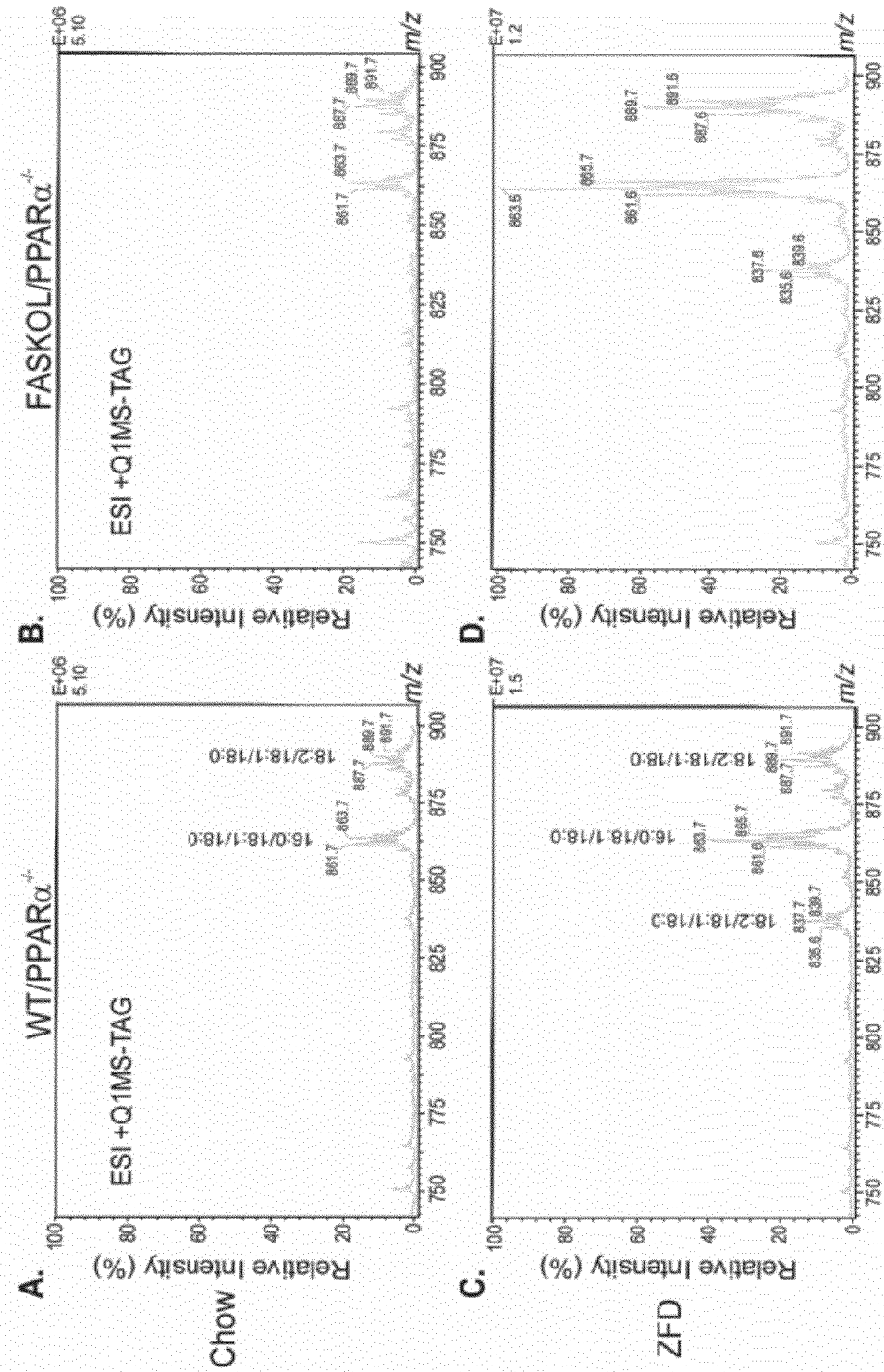
FIG. 8 are representative positive ion (+Q1) ESI/MS analyses of triacylglycerol (TAG) species in the excess FLAG®-ELUTED hepatic nuclear extracts obtained from either chow (FIGS. 8A and 8B) or zero fat (ZFD) (FIGS. 8C and 8D) fed WT and FASKOL mice on a PPARα null background infected with the AdFLAG®-PPARα adenovirus. The mass-to-charge (m/z) ratios denote the molecular identity of the corresponding TAGs in each peak.
Figure 9:
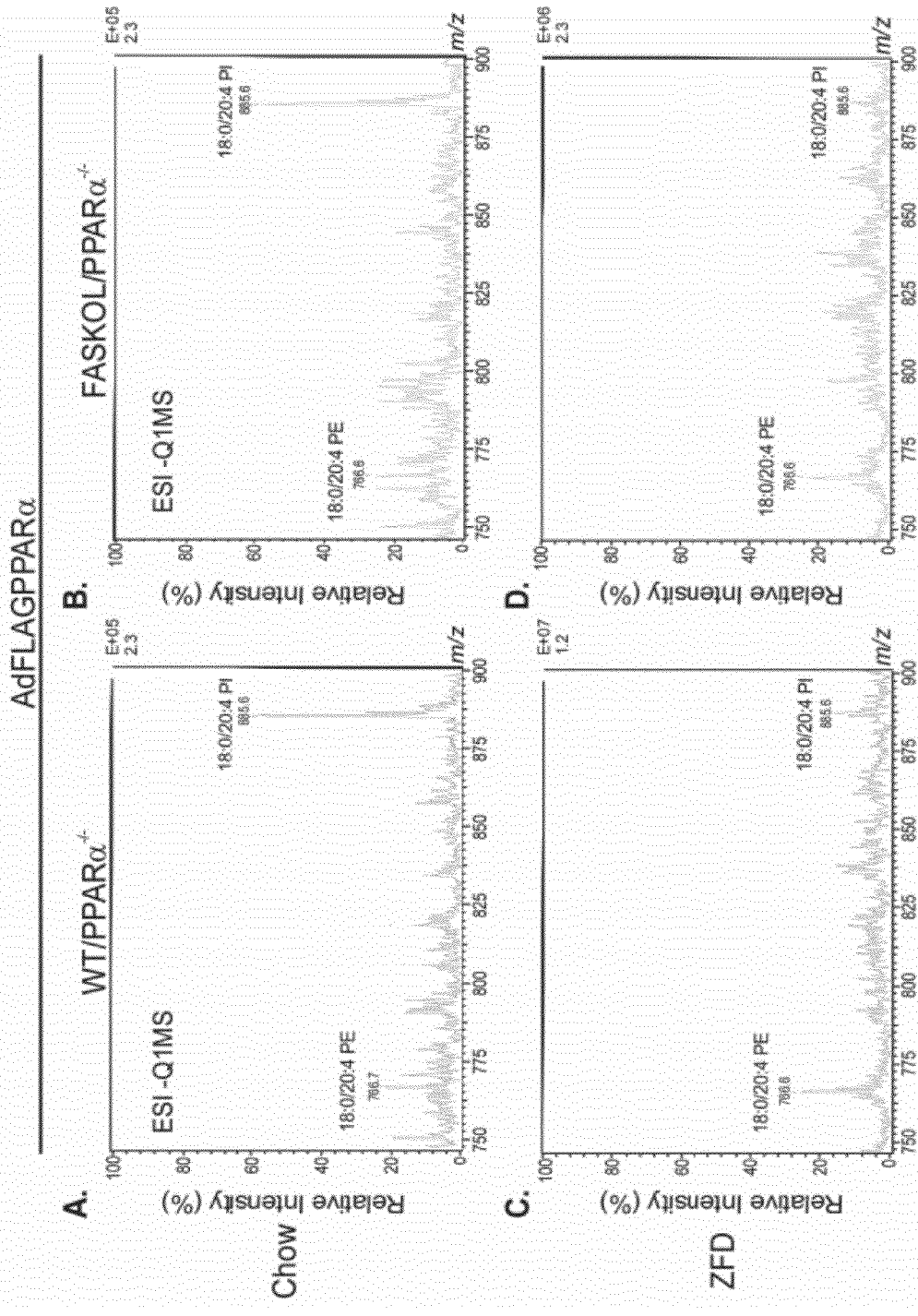
FIG. 9 illustrates representative negative ion (−Q1) ESI/MS analyses of nuclear phospholipids in the excess FLAG®-eluted hepatic nuclear extracts obtained from either chow (FIGS. 9A and 9B) or zero fat (ZFD) (FIGS. 9C and 9D) fed WT and FASKOL mice on a PPARα null background infected with the AdFLAG®-PPARα adenovirus. The fragment ion at m/z 766 and 885 depict 18:0/20:4 phosphatidylethanolamine (PE) and phosphatidylinositol (PI), respectively.
Figure 10:
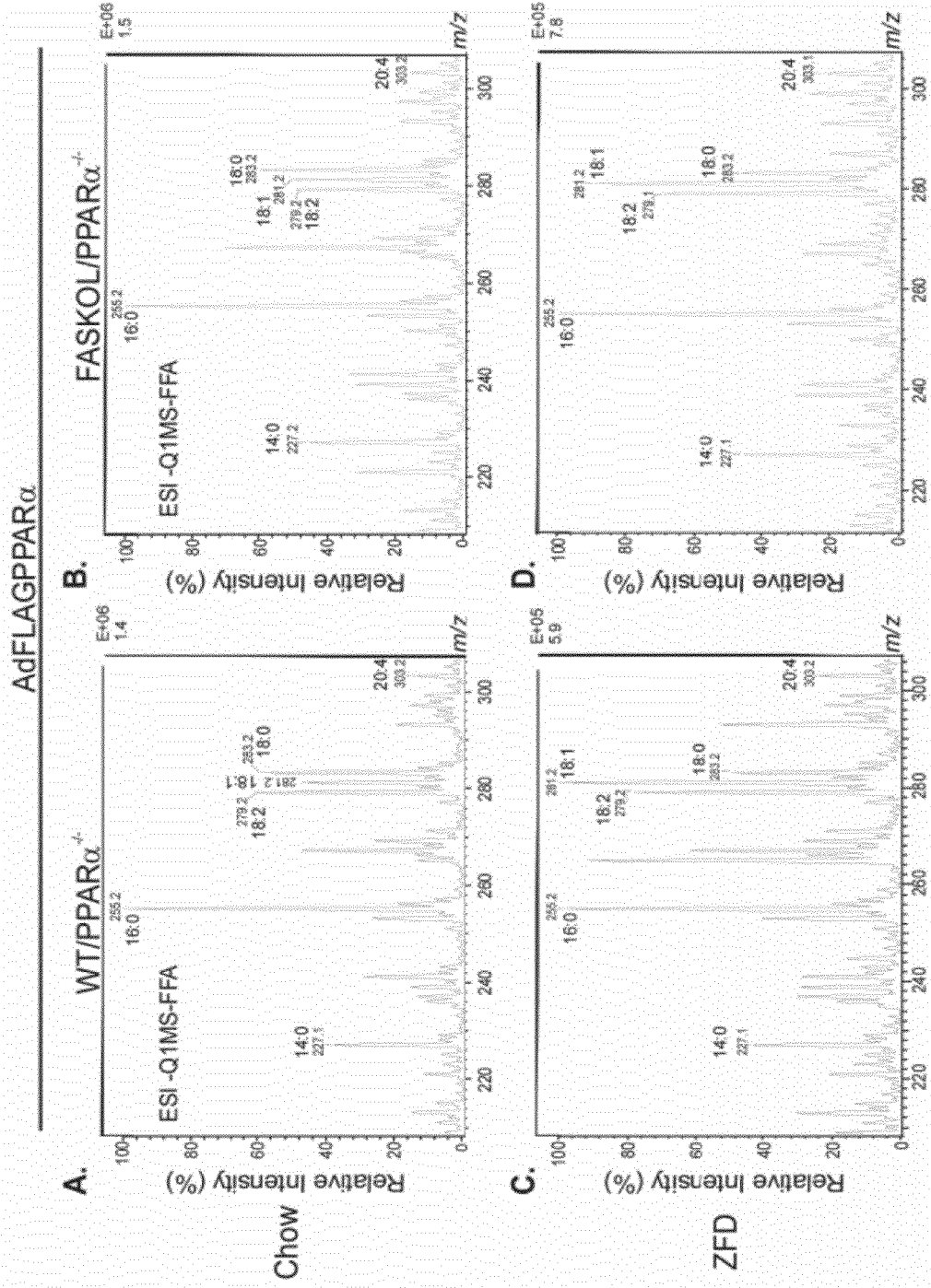
FIG. 10 illustrates representative negative ion (−Q1) ESI/MS analyses of nuclear free fatty acids (FFA) in the excess FLAG®-eluted hepatic nuclear extracts obtained from either chow (FIGS. 10A and 10B) or zero fat (ZFD) (FIGS. 10C and 10D) fed WT and FASKOL mice on a PPARα null background infected with the AdFLAG®-PPARα adenovirus. Fatty acids are identified by their corresponding m/z ratios as depicted in each of the profiles.
Figure 11:
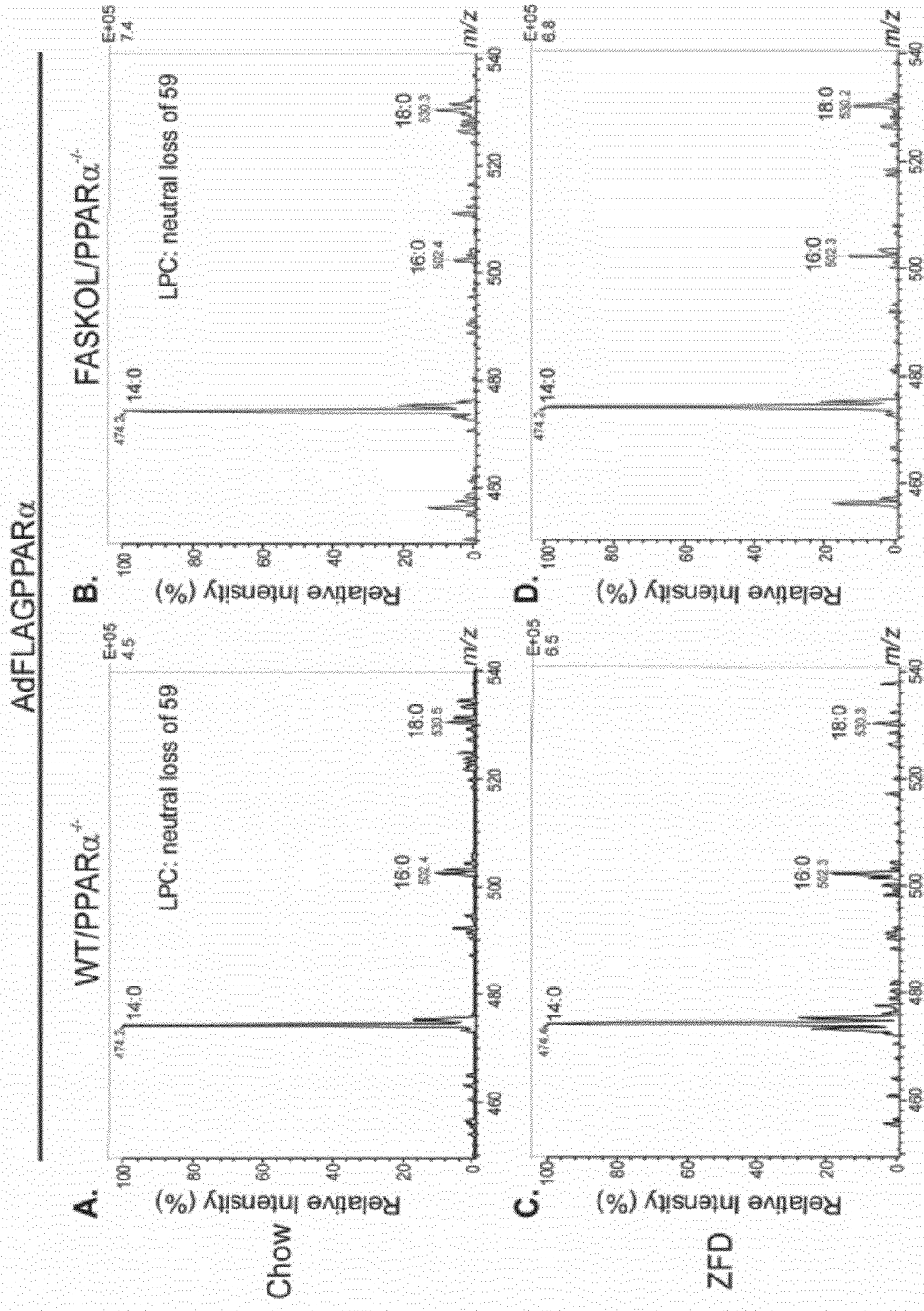
FIG. 11 illustrates representative positive ion ESI/MS analyses of lithiated adducts of hepatic nuclear phospholipids to monitor the loss of 59 [$N(CH_3)_3$], which identifies parent ions that contain the lysophosphatidylcholine (LPC) headgroup in the excess FLAG®-eluted hepatic nuclear extracts obtained from either chow (FIGS. 11A and 11B) or zero fat (ZFD) (FIGS. 11C and 11D) fed WT and FASKOL mice on a PPARα null background infected with the AdFLAG®-PPARα adenovirus. The fatty acid moieties in LPC are identified by their corresponding m/z ratios as depicted in each of the profiles.

Absence of the Detection of Fatty Acids or Triglycerides Bound to PPARα that were Consistent with an FAS-Dependent Authentic Endogenous PPARα Ligand FAS dependence of fatty acids and triglycerides was assessed by isolating PPARα from mice with and without FAS deficiency and from animals fed chow as well as a high carbohydrate, zero fat diet (ZFD), since carbohydrates induce FAS expression. PPARα triglyceride binding was increased in both wild type and FAS-deficient livers (FIG. 8). This was more pronounced in the latter, consistent with the hepatic steatosis that occurs with zero fat diet feeding in FASKOL mice. There were no genotype or diet effects on binding to PPARα for species of phosphatidylethanolamine or phosphatidylinositol (FIG. 9), common fatty acids (FIG. 10), or lysophosphatidylcholine (FIG. 11).

Example 2

The primary objective was to establish the identity of the phospholipid 1-palmitoyl-2-oleoyl-sn-glycerol-3-phosphocholine (16:0/18:1-GPC) as a FAS-dependent physiologically relevant endogenous PPARα ligand. A strategy to employ the use of mass spectrometry analysis of lithiated adducts of glycerophosphocholine lipids from hepatic nuclear extracts was developed to accomplish this objective.

Electrospray Ionization Mass Spectrometry

Phosphatidylcholine (GPC), lysophosphatidylcholine (LPC), sphingomyelin (SM), and ceramide (CM) were analyzed as Li+ adducts by positive ion ESI/MS on a Finnigan (San Jose, Calif.) TSQ-7000 triple stage quadrupole mass spectrometer with an ESI source controlled by Finnigan ICIS software. Lipids were dissolved in methanol/chloroform (2/1, v/v) containing LiOH (10 pmol/μl), infused with a Harvard syringe pump, and analyzed as described (J Am Soc Mass Spectrom 9, pp. 516-526, 1998; J Am Soc Mass Spectrom 11, pp. 437-449, 2000; J Am Soc Mass Spectrom 14, pp. 352-363, 2003; J Mass Spectrom 38, pp. 752-763, 2003). Positive ion ESI/MS analyses of lithiated adducts of hepatic nuclear phospholipids were performed to monitor neutral loss of 189 [$LiPO_4(CH_2)_2N(CH_3)_3$], which identifies parent ions that contain the phosphocholine head-group in lipid mixtures.

Representative profiles of GPC species in chow fed WT and FASKOL mice on a PPARα null background infected with AdGFP are shown in FIGS. 2A and 2C and those infected with AdFLAG-PPARα are shown FIGS. 2B and 2D. Representative profiles of GPC species in zero fat diet (ZFD) fed WT and FASKOL mice on a PPARα null background infected with AdGFP are shown in FIGS. 2E and 2G and those infected with AdFLAG-PPARα are shown in FIGS. 2F and 2H. Insets in FIGS. 2B, 2D, 2F, and 2H depict the fragment ion at mass-to-charge ratio (m/z) 766 as the specific GPC species that is both PPARα and FAS dependent. Quantification of the relative abundance of the m/z 766 ion with respect to genotype (W/P, WT on PPARα null background; F/P, FASKOL on PPARα null background) and diet (chow and ZFD) is indicated in FIG. 2I. Each bar represents mean±SEM from 3 independent experiments with 4-6 mice in each group per experiment. *, P<0.05 vs. corresponding W/P control; **, P<0.05.

For tandem mass spectrometry, precursor ions selected in the first quadrupole were accelerated into a chamber containing argon to induce collisionally-activated dissociation, and product ions were analyzed in the final quadrupole. Constant neutral loss scanning was performed to monitor GPC [M+Li]+ ions that undergo loss of 183 or 189 (phosphocholine or its Li+ salt) and similar scans were performed to monitor LPC and SM [M+Li]+ ions that undergo loss of 59 (trimethylamine) and to monitor CM [M+Li]+ ions that undergo loss of 48 (water plus formaldehyde). Intensities of ions for internal standards were compared to those of ions for endogenous species followed by interpolation using calibration curves. Glycerophospho-ethanolamine, -glycerol, -serine, and -inositol, were analyzed as [M-H]− ions by negative ion ESI/MS(/MS) relative to internal standards (Endocrinology 139, pp. 4073-4085, 1998) and their tandem spectra were obtained.

Tandem mass spectrometry analysis establishes the identity of the phospholipid species as a phosphatidylcholine, 1-palmitoyl-2-oleoyl-sn-glycerol-3-phosphocholine (16:0/18:1-GPC). FIG. 3A illustrates the fragmentation pattern upon collisionally-activated dissociation of the ion of m/z 766, which corresponds to the lithiated adduct [MLi$^+$] of 16:0/18:1-GPC. Neutral loss of trimethylamine [MLi$^+$−59] yields an ion at m/z 707. Ions at m/z 583 [MLi$^+$−183] and m/z 577 [MLi$^+$−189] reflect net loss of [$HPO_4(CH_2)_2N(CH_3)_3$] and of [$LiPO_4(CH_2)_2N(CH_3)_3$], respectively. Losses of 59, 183, and 189 are common to the tandem spectra of all GPC-Li$^+$ species, regardless of the fatty acid components, so these ions identify the phosphocholine head-group. FIG. 3B shows ions at m/z 510, m/z 504, and m/z 451 reflecting neutral loss of palmitic acid [MLi$^+$−256], loss of the lithium salt of palmitate [MLi$^+$−262], and loss of trimethylamine plus palmitic acid [MLi$^+$−315], respectively. The spectra also show ions reflecting the loss of oleic acid (m/z 484), loss of the lithium salt of oleate (m/z 478), and loss of trimethylamine plus oleic acid (m/z 425). Relative abundances of the ions at m/z 425 [MLi$^+$−(59+oleic acid)] and 451 [MLi$^+$−(59+palmitic acid)] in FIG. 3B indicate that palmitate and oleate are the sn-1 and sn-2 substituents, respectively, because the abundance of the ion reflecting loss of trimethylamine plus the sn-1 substituent always exceeds that of the ion reflecting loss of trimethylamine plus the sn-2 substituent (J Am Soc Mass Spectrom 9, pp. 516-526, 1998). FIG. 3C shows a schematic diagram of the structure of the PPARα ligand.

Example 3

The primary objective was to establish the physiological relevance and binding specificity of 1-palmitoyl-2-oleoyl-sn-glycerol-3-phosphocholine (16:0/18:1-GPC) to PPARα. Competitive inhibition and DNA binding activity was employed to address this objective.

DNA Binding Activity

Cos-7 cells maintained in DMEM containing 10% fetal bovine serum were transiently transfected with 2 μg of wild type- and DBD-mutant-PPARα plasmids using FuGENE6 (Roche Diagnostics, Indianapolis, Ind.) as described (Cell Metab 5, pp. 59-72, 2007). Nuclear extract DNA binding activity was determined using the PPARα transcription factor assay kit (Cayman Chem, Inc., Ann Arbor, Mich.).

Binding Assays

Binding of 16:0/18:1-GPC and known agonists to the ligand binding domain (LBD) of PPARα in the presence of various peptide motifs was determined by ALPHAS-CREEN™ assay (Proc Natl Acad Sci USA 105, pp. 5034-5039, 2008). Experiments used 100 nM receptor LBD, purified as 6× His tag fusion proteins (Mol Cell 17, pp. 491-502, 2005), and 20 nM of N-terminal biotinylated CBP1 peptide or other coactivator peptides in the presence of 5 µg/ml donor and acceptor beads in 50 mM MOPS (pH 7.4), 100 mM NaCl, and 0.1 mg/ml BSA for 90 min at 25° C. Signals were generated in the absence or the presence of ligand. Identical experiments were performed using the PPARδ and PPARγ LBDs.

In Vivo Competitive Inhibition Experiment Using Wy14,643

If 16:0/18:1-GPC is the endogenous PPARα ligand, it should be possible to competitively inhibit its binding with a known ligand in living mice. This was demonstrated by administering 50 µg/g of Wy14,643, a dose known to rapidly activate PPARα (Cell Metab 1, pp. 309-322, 2005), at time 0, followed by subsequent sacrifice of animals for isolation of PPARα-bound lipids. The putative ligand was displaced from PPARα within minutes of treatment with the known ligand, both in the setting of chow (FIG. 4A-D) as well as zero fat diet feeding (FIG. 4E-H). Note the rapid decrease in abundance for m/z 766 (representing 16:0/18:1-GPC) relative to the invariant m/z 764 and the increased abundance of m/z 766 at 0 minutes with zero fat diet compared to chow diet. Quantitation of peak abundance for independent experiments is presented in FIG. 4I.

The in vivo displacement of the endogenous PPARα ligand 16:0/18:1-GPC by the PPARα agonist Wy14,643 was assessed by electrospray ionization mass spectrometry (ESI/MS) Analysis. ESI/MS total positive ion profiles were used to monitor neutral loss of 189 from lithiated adducts of GPC species in excess FLAG®-eluted hepatic nuclear extracts obtained from Wy14,643 (Wy)-treated mice. Representative ESI/MS scans of GPC species at different time intervals following an intraperitoneal injection of 50 µg/g. Wy14,643 in chow fed WT mice on a PPARα null background injected with AdFLAG-PPARα adenovirus are shown in FIGS. 4A-D. Similarly, representative ESI/MS scans of GPC species at different time intervals following an intraperitoneal injection of 50 µg/g Wy14,643 in ZFD fed mice are shown in FIGS. 4E-H. Insets in FIGS. 4A-H depict the ion at m/z 766 (16:0/18:1-GPC) that is time-dependently competed away with Wy14,643 while quantification of the relative abundance of the peak abundance of m/z 766 ion in response to Wy14,643 is shown in FIG. 4I. Graphs represent mean±SEM from two independent experiments with 4-5 mice in each group per experiment. The putative ligand was displaced from PPARα within minutes of treatment with the known ligand, both in the setting of chow (FIG. 4A-D) as well as zero fat diet feeding (FIG. 4E-H). There is also a rapid decrease in abundance for m/z 766 (representing 16:0/18:1-GPC) relative to the invariant m/z 764 and the increased abundance of m/z 766 at 0 minutes with zero fat diet compared to chow diet.

Modified In Vivo Competitive Inhibition Experiment Using Wy14,643 and a PPARα Molecule with a Defective DNA Binding Domain To address the concern that lipid loss could represent Wy14,643-accelerated metabolism as opposed to displacement of the ligand, 1-palmitoyl-2-oleoyl-sn-glycerol-3-phosphocholine (16:0/18:1-GPC) from its binding site on PPARα, an in vivo competitive inhibition experiment using a PPARα molecule with a defective DNA binding domain (see FIG. 5A) was employed. Immunoblot analysis of Cos-7 cells transfected with empty vector, wild type (WT), or DBD-mutant (ΔDBD) PPARα plasmids using anti-PPARα and proliferating cell nuclear antigen (PCNA) antibodies was done. Gels are representative of three independent experiments (see FIG. 5B). Two cysteine residues conserved in all PPAR family members were mutated to alanines in PPARα (FIG. 5A). Mutation of these residues in PPARδ abolishes DNA binding activity (Proc Natl Acad Sci USA 99, pp. 2613-2618, 2002). The mutation of C119A, C122A disrupts PPARα DNA binding activity (see FIG. 5C). Cos-7 cells were transfected and DNA binding activity was assayed. Graphs represent mean±SEM of experiments performed in triplicate. *, P<0.05 vs. empty vector. #, P<0.05 vs. WT control. Representative ESI/MS total positive ion profiles monitoring neural loss of 189 from lithiated adducts of GPC species in FLAG-eluted hepatic nuclear extracts obtained from chow fed WT and FASKOL mice on a PPARα null background infected with adenovirus AdGFP are shown in FIGS. 5D and 5F and those infected with adenovirus AdFLAG$^{-\Delta DBD}$PPARα are shown in FIGS. 5E and G. Insets in FIGS. 5E and 5G depict the ion at m/z 766 (16:0/18:1-GPC) as the specific phospholipid species that is FAS dependent while quantification of the relative abundance of the m/z 766 ion in response to control and mutant adenoviral injections in W/P (WT on PPARα null background) and F/P (FASKOL on PPARα null background) mice is shown in FIG. 5H. Each bar represents the mean±SEM from three independent experiments with 4-6 mice in each group per experiment. *, P<0.05 vs. corresponding W/P control. Representative neutral loss of 189 ESI/MS scans of GPC species at different time intervals following intraperitoneal injection of 50 µg/g Wy14,643 in chow fed WT mice on a PPARα null background injected with AdFLAG-$^{\Delta DBD}$ PPARα adenovirus is shown in FIGS. 5I-L. Insets in FIGS. 5I-L indicate that the ion at m/z 766 (16:0/18:1-GPC) is time-dependently competed away from the DBD defective PPARα with Wy14,643. Quantification of the relative abundance of the m/z 766 ion in response to Wy14,643 administration in WT mice on a PPARα null background injected with AdFLAG-$^{\Delta DBD}$ PPARα adenovirus is shown in FIG. 5M. Graphs represent mean±SEM from two separate experiments with 3-4 mice in each group per experiment.

Figure 5:
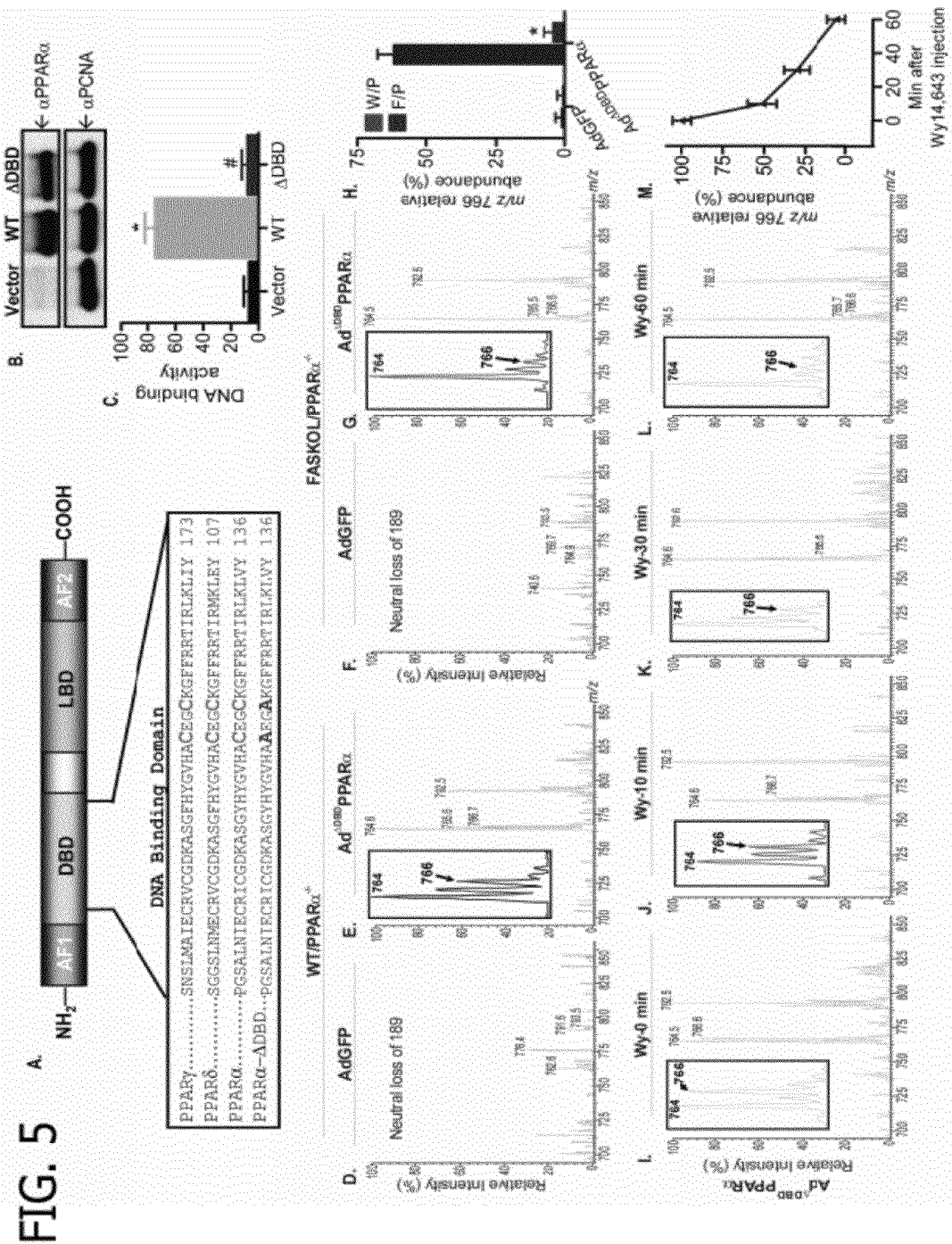
FIG. 5 illustrates the results of an in vivo competitive inhibition experiment using a PPARα molecule with a defective DNA binding domain.
Figure 6:
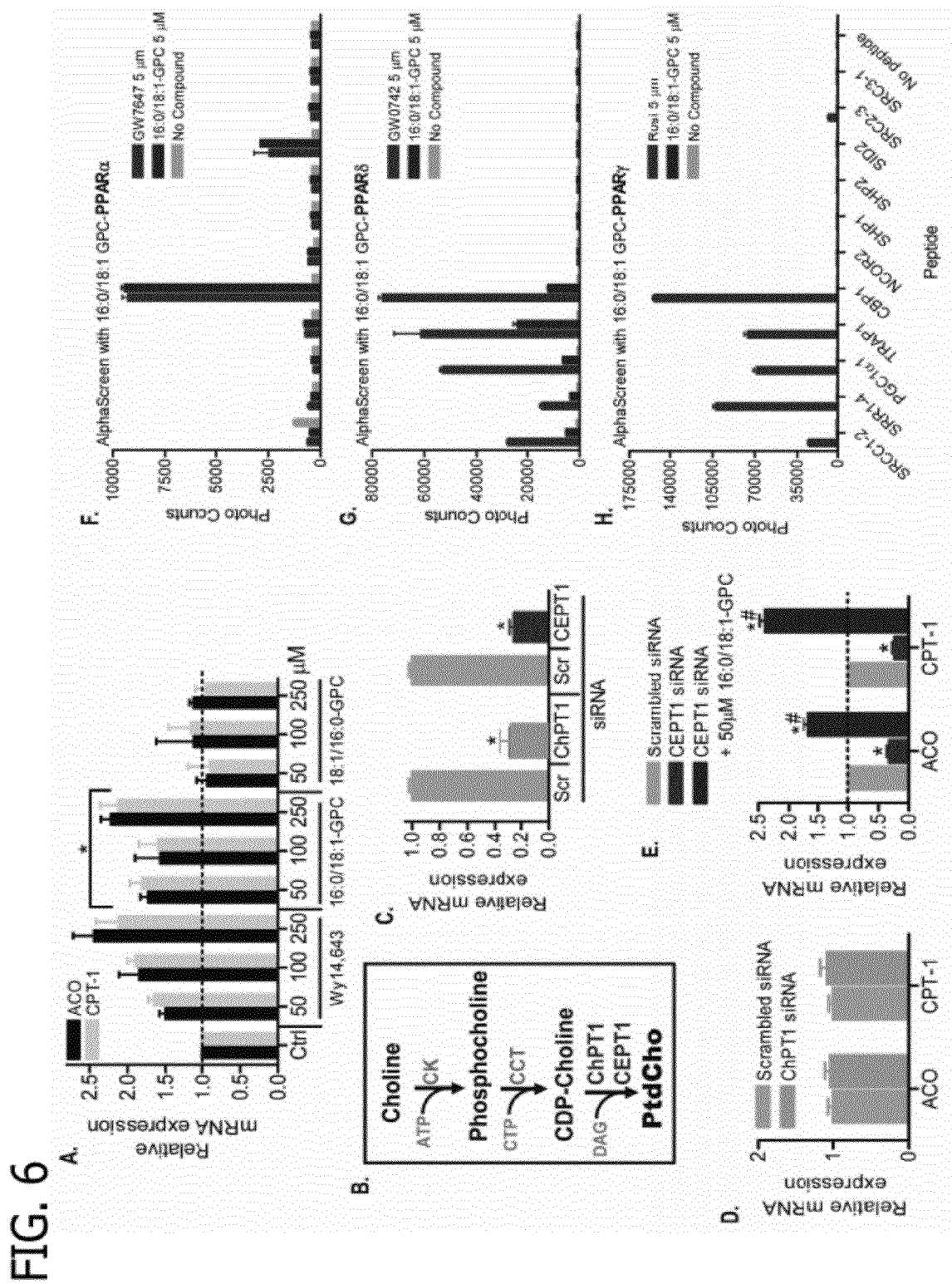
FIG. 6 illustrates gene expression and relevant binding assays for PPAR α-dependent or target genes acyl-CoA oxidase (ACO or AOX) and carnitine palmitoyl transferase I (CPT-1).

While the rapid decline in signal with Wy14,643 treatment could represent displacement of the ligand from its binding site on PPARα, Wy14,643 activates lipid oxidation, meaning that lipid loss could instead represent accelerated metabolism. To address this, we repeated the in vivo competitive inhibition experiment using a PPARα molecule with a defective DNA binding domain (FIG. 5) The PPARα molecule with a defective DNA binding domain, ΔDBD-PPARα, should retain ligand binding yet be incapable of increasing transcriptional programs promoting lipid metabolism. Adenoviral expression of this mutated protein resulted in similar levels of protein as wild type PPARα (FIG. 5B), and DNA binding was verified to be impaired with this mutant (ΔDBD in FIG. 5C). Mice were infected with AdGFP (as a control) or Ad-ΔDBD-PPARα in the presence (WT/PPARα-/-) or absence (FASKOL/PPARα-/-) of FAS and lipids from affinity-purified nuclear extracts were subjected to mass spectrometry (FIG. 5D-H). Nonspecific binding was minimal (FIG. 5D, F), and m/z 766 (representing 16:0/18:1-GPC) was detected with the mutant PPARα in the presence of FAS (FIG. 5E, arrow) with a substantial decrease noted in the absence of FAS (FIG. 5G, arrow). As seen with wild type PPARα, m/z 766 was competed away from ΔDBD-PPARα within minutes of administration of Wy14,643 to mice (FIG. 5I-L). Competitive inhibition data from independent experiments are presented in FIG. 5M. These results suggest that 16:0/18:1-GPC binding to PPARα is FAS-dependent and involves a binding site that is also occupied by a known PPARα activator.

Example 4

The primary objective was to establish that 1-palmitoyl-2-oleoyl-sn-glycerol-3-phosphocholine (16:0/18:1-GPC)

induces the expression of PPARα-dependent genes including but not necessarily limited to acyl-CoA oxidase (ACO) and carnitine palmitoyl transferase I (CPT-I) in cultured cells.

RT-PCR gene expression analysis and binding assays were employed to address this objective. Wy14,643, 16:0/18:1-GPC, and 18:1/16:0-GPC on PPARα target gene (ACO and CPT-1) expression was measured by quantitative RT-PCR in Hepa 1-6 cells treated for 24 h as in FIG. 6A. Results are mean±SEM of 9 separate experiments. *, P<0.05 compared to control (Ctrl, 80% PBS/20% DMSO).

Mouse Hepatocytes Used to Monitor Gene Expression

The C57BL/6 mouse hepatoma cell line Hepa 1-6 (ATCC, CRL-1830) was expanded in DMEM with 10% fetal bovine serum. For experiments, cells were cultured to 50-60% confluence, washed twice with PBS, and the medium was changed to serum-free DMEM supplemented with the various types and concentrations of phosphatidylcholine (sonicated to homogeneity in PBS/1% ethanol/4% fatty acid-free BSA), Wy14,643 (dissolved in 80% PBS/20% DMSO), or vehicle-only solutions. 24 h later, cells were washed, RNA prepared, and ACO and CPT-1 expression levels were determined by quantitative RT-PCR (see FIG. 6). For siRNA experiments, 50-60% confluent cells were treated with siRNAs or their scrambled controls (all diluted in PBS) for 72 h. Following the 72 h siRNA treatment, another set of cells received 16:0/18:1-GPC (using a concentration based on dose-response experiments) for an additional 24 h. Stealth™ siRNA oligonucleotides were used to inhibit the gene expression of mouse ChPT1 (GGAGGAGCAACAAUGUGGGAC-UAUA) (SEQ ID NO: 1) and CEPT1 (UGGCAGUGAUUG-GAGGACCACCUUU) (SEQ ID NO: 2) were from Invitrogen (Carlsbad, Calif.).

Restoration of PPARα-Dependent Gene Expression in Cultured Cells and Quantitative RT-PCR-Based Gene Expression Incubation of cultured mouse hepatoma cells with exogenous 1-palmitoyl-2-oleoyl-sn-glycerol-3-phosphocholine (the FAS-dependent phosphatidylcholine species) increased expression of both ACO and CPT-I to a similar degree as equimolar amounts of the known PPARα activator Wy14,643 (FIG. 6A).

Endogenous phosphatidylcholine also affects PPARα-dependent genes. Endogenous synthesis of phosphatidylcholine occurs mostly through the Kennedy pathway (FIG. 6B), which involves the successive action of choline kinase (CK) and CTP:phosphocholine cytidylyltransferase (CCT) to yield CDP-choline (Biochim Biophys Acta 1733, pp. 53-66, 2005). This substrate reacts with diacyglycerol (DAG) to yield phosphatidylcholine (PtdCho) through the action of one of two enzymes, choline phosphotransferase 1 (ChPT1), found in the Golgi, and choline-ethanolamine phosphotransferase-1 (CEPT1), found in the nucleus as well as the endoplasmic reticulum (Mol Biol Cell 13, pp. 3148-3161, 2002). 1-Palmitoyl-2-Oleoyl-sn-Glycero-3-Phosphocholine (PC16:0/18:1) and its regioisomer, 1-Oleoyl-2-Palmitoyl-sn-Glycero-3-Phosphocholine (PC18:1/16:0) were obtained from Avanti Polar Lipids (Alabaster, Ala.). siRNA-mediated knockdown was achieved in cultured mouse hepatoma cells (FIG. 6C), followed by assessment of PPARα-dependent genes.

Stealth™ siRNA oligonucleotides were used to inhibit the gene expression of mouse ChPT1 (GGAGGAGCAACAAU-GUGGGACUAUA) (SEQ ID NO: 1) and CEPT1 (UG-GCAGUGAUUGGAGGACCACCUUU) (SEQ ID NO: 2) were from Invitrogen (Carlsbad, Calif.). The effect on ChPT1 and CEPT1 mRNA levels normalized to L32 ribosomal mRNA in response to 72 h treatment with corresponding siRNAs and scrambled (Scr) controls in Hepa 1-6 cells is shown in FIG. 6C. The effect of 72 h treatment with scrambled and ChPT1 siRNAs on PPARα target genes (ACO and CPT-1) by RT-PCR normalized to L32 ribosomal mRNA in Hepa 1-6 cells is shown in FIG. 6D. The effect of 72 h treatment with scrambled and CEPT1 siRNAs on ACO and CPT-1 message levels in Hepa 1-6 cells is shown in FIG. 6E. Expression of ACO and CPT-1 was also assessed 24 h after addition of 50 μM 16:0/18:1-GPC in a subset of Hepa 1-6 cells previously treated with CEPT1 siRNA. mRNA levels are normalized to control L32 ribosomal mRNA. For FIGS. 6C-E, graphs represent mean±SEM of three separate experiments with each group in triplicate. *, P<0.05 compared to scrambled controls. #, P<0.05 compared to CEPT1 siRNA treated cells. FIGS. 6F-H show the binding of various peptide motifs to the purified PPARα (FIG. 6F), PPARδ (FIG. 6G), and PPARγ (FIG. 6H) LBD in the presence of 5 μM of the corresponding PPAR agonist or 16:0/18:1-GPC as measured by AlphaScreen assays. The background signals of either the respective LBDs or the peptides alone, or without addition of the ligand/agonist (no compound), are all less than 800. The results are averages of two separate experiments.

Total RNA was extracted from Hepa 1-6 cells and liver using Trizol (Invitrogen) and treated with DNase I (RNase-free, Roche Molecular Biochemicals). Reverse transcription to cDNA and real-time quantitative PCR were performed using previously published procedures and primer-probe sequences for ACO and CPT-1 (Chakravarthy et al., 2005). RT-PCR for ChPT1 and CEPT1 was performed using the following primer-probe sets: ChPT1 (Forward, 5'-TGCT-CATCTTCTACTGCCCTACAG-3' (SEQ ID NO: 3); Reverse, 5'-AGAGTCCCAGGGCACATAAAAG-3' (SEQ ID NO: 4); Probe, 5'-CACGGAGGAGGCACCATACTG-GACAT-3' (SEQ ID NO: 5)); CEPT1 (Forward, 5'-TGCTG-GACGGTCCCTTCTC-3' (SEQ ID NO: 6); Reverse, 5'-ATC-CATGAGGGTACTCTTCCAACT-3' (SEQ ID NO: 7); Probe, 5'-CCCTTAATGCAAGGATACTGGGAATGGC-3' (SEQ ID NO: 8)). RNA not subjected to reverse transcription was included in each assay as a negative control. PCR reactions were performed in triplicate using an Applied Biosystems 7700 instrument. Relative mRNA levels were calculated using both the comparative $C_T$ and standard curve methods normalized to ribosomal protein L32, an invariant internal control. Amplified bands were sequenced to verify their identity.

Inactivation of ChPT1, the Golgi enzyme, had no effect on ACO or CPT-1 (FIG. 6D). However, knockdown of CEPT1, the nuclear/ER enzyme, decreased PPARα-dependent genes, and effect that was rescued by exogenous 16:0/18:1-GPC (FIG. 6E), consistent with the notion that endogenous PtdCho activates PPARα and that FAS-dependent 16:0/18:1-GPC is the endogenous PPARα ligand. This indicates that 1-palmitoyl-2-oleoyl-sn-glycerol-3-phosphocholine (16:0/18:1-GPC) activation of PPARα induces expression of genes involved in fatty acid metabolism such as acyl-CoA oxidase and carnitine palmitoyl transferase I (ACO and CPT-I).

16:0/18:1-GPC also appears to restore PPARα-dependent gene expression including, but not necessarily limited to, acyl-CoA oxidase and carnitine palmitoyl transferase I in cultured cells missing the choline-ethanolamine phosphotransferase-1 (CEPT1) gene (also referred to as a knockdown of CEPT1). This also would seem to indicate that 16:0/18:1-GPC activates PPARα and that FAS-dependent 16:0/18:1-GPC is an endogenous PPARα ligand (see FIG. 6).

It appears that 16:0/18:1-GPC is a configuration-specific physiologically-relevant endogenous PPARα ligand. The precise configuration of fatty acids within phosphocholine affects ligand activation, and generally 16:0/18:1-GPC is the only FAS-dependent phosphocholine discovered to be bound to PPARα. In particular, it was found that 16:0/18:1-GPC induces PPARα-dependent gene expression in cultured hepatocytes, but its regioisomers, and in particular the regioisomer 18:1/16:0-GPC, a molecule having essentially the same structure but for the reversal of the position of the fatty acids, does not induce PPARα-dependent gene expression in cultured hepatocytes (FIG. 6A). Furthermore, binding of the 16:0/18:1-GPC to PPARα appears to be highly specific, as 16:0/18:1-GPC does not appear to bind to PPARγ (see, FIGS. 6F, 6G, and 6H) and its interaction with PPARδ is insubstantial in comparison to the interaction between PPARδ and the PPARδ activator GW0742 (FIG. 6G).

It has been reported that some of naturally occurring free fatty acids reported to act as ligands of PPARα do not bind with sufficient affinity to PPARα in comparison to a prototypical synthetic fibrate agonist, Wy14,643, within the context of alcohol-induced fatty liver disease. (Journal of Lipid Research, 41(11) 1801-1807, 2000; Molecular Endocrinology 11, 779-791, 1997; European Journal of Clinical Investigation, 34, 429-435, 2004; Journal of Biological Chemistry, 278 (30), 27997-28004, 2003). To the contrary, it has been discovered, as described herein, that 16:0/18:1-GPC binds with sufficient affinity to PPARα comparable to Wy14,643 (FIG. 6A).

Example 5

The primary objective was to provide in vivo evidence that 1-palmitoyl-2-oleoyl-sn-glycerol-3-phosphocholine (16:0/18:1-GPC) activates PPARα by inducing the expression of PPARα-dependent genes including but not necessarily limited to acyl-CoA oxidase and carnitine palmitoyl transferase I (ACO and CPT-I) in a mouse model representative of disorders of the liver including human fatty liver disease or hepatic steatosis. Secondary objectives were to assess overall lipid content and trigylceride levels in liver tissue after infusion of 1-palmitoyl-2-oleoyl-sn-glycerol-3-phosphocholine (16:0/18:1-GPC) into the mice as a viable indication of the therapeutic efficacy of 16:0/18:1-GPC ligand in treating fatty liver disease or hepatic steatosis.

Establishing Conditions for Portal Vein Infusion of 16:0/18:1-GPC

Small doses of fatty acids even for a short duration can exert striking metabolic effects. For example, portal venous infusion of oleate at 150 nmol/min for just 24 h induces hypertension and decreases insulin sensitivity (Benthem et al., 2000). Given the relatively high flow rate (1.5 ml/min) in the portal vein (Grekin et al., 1995), injection into this vessel leads to a direct and short transit time into the liver, thereby minimizing binding of lipids by albumin.

There are few studies regarding the specific use of phosphatidylcholine (PtdCho) infusions. In humans, PtdCho was given either intravenously at a total dose of 2 g/day for 3 days (Cantafora et al., 1992) or orally at a total dose of 2 g/day for 12 wks (Stremmel et al., 2007). In rats, PtdCho was infused at a rate of 9 μmol/h into the duodenum for 6 h (=40 mg) (Mansbach and Dowell, 1993). We are not aware of studies that report PtdCho infusion directly into the portal vein.

Figure 12:
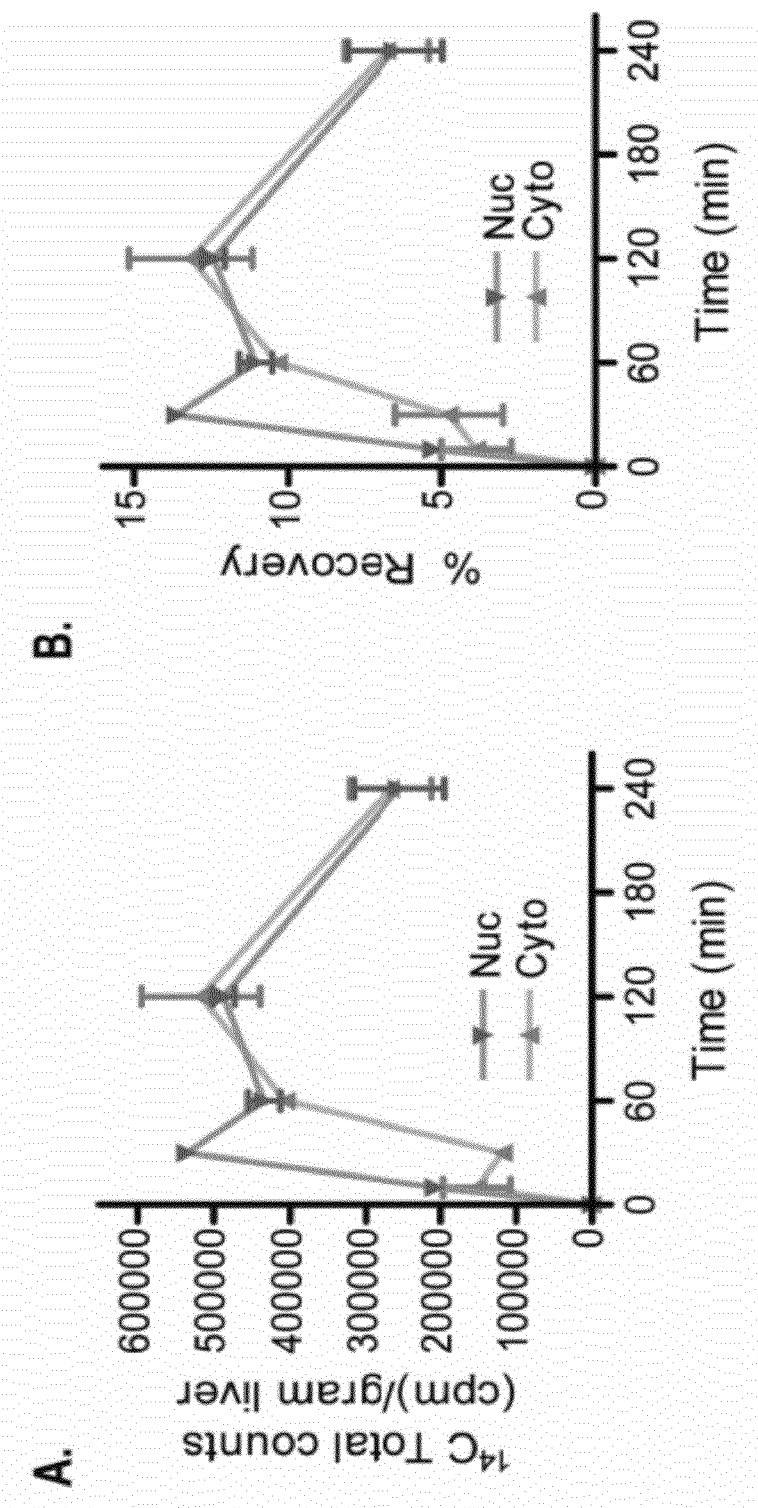
FIG. 12 graphically illustrates graphical kinetic assays for $^{14}$C-16:0/18:1-GPC.

We therefore extrapolated the doses in mice taking into account the direct intraportal route, and tested doses ranging from 0.1 mg/day to 10 mg/day based on a 25 g mouse. We found that rapid infusion (<1 min) was optimal and that the lowest dose causing increased expression of the PPARα target gene acyl CoA oxidase was 10 mg/kg. Larger doses and slower infusion rates resulted not only in poor solubility but also death due to portal vein thrombosis. Optimal dosing frequency was determined based on kinetic data obtained by injection of $^{14}$C-labeled 16:0/18:1-GPC (American Radiochemicals, St. Louis) into the portal vein of 057/BL6 mice as shown in FIG. 12. Following a single injection into the portal vein (1.9 μCi/mouse), total counts from both cytoplasmic and nuclear fractions were obtained (FIG. 12A). Using standard pharmacokinetic equations (Hardman et al., 2001), a dosing interval of 8.7 hours was calculated, indicating an optimal dosing frequency of three times a day.

Maximum recovery of the injected $^{14}$C-labeled compound ranged from 10-15% of the total injected dose in nuclear fractions (FIG. 12B). While it is possible that the recovered counts might not represent the intact 16:0/18:1-GPC molecule, indirect evidence in Caco-2 cells suggests that labeled PtdCho is not rapidly hydrolyzed (Treede et al., 2007). Assuming that the PtdCho species injected into the portal vein of mice remained stable for 30 min, peak nuclear recovery exceeds that seen in Caco2 cells (Treede et al., 2007). This likely represents a pharmacological dose because 16:0/18:1-GPC is a minor phosphatidylcholine species in liver (Hsu et al., 1998).

Hepatic Portal Vein Infusion

Portal veins were cannulated as described (Physiol Behav 65, pp. 885-887, 999). The catheter (0.025 mm OD×0.012 mm ID, Braintree Scientific), prefilled with 55% (w/v) polyvinylpyrrolidone (Sigma) in heparin (100 IU/ml saline) to prevent clotting, was anchored to the abdominal wall, and its free end was inserted under the skin of the mice and tunneled to a small midline incision slightly distal to the scapula on the back. Body weight and food intake returned to baseline levels (usually by day 3) before experiments. Starting on post-op day 4, animals were fed a zero fat diet (TD 03314, Harlan Teklad) for 5 days, which induces modest to severe fatty liver or hepatic steatosis in C57BL/6 and PPARα$^{-/-}$ mice, respectively. During this period, animals received three intraportal infusions a day of either 10 mg/kg 1-palmitoyl-2-oleoyl-sn-glycerol-3-phosphocholine (16:0/18:1-GPC) sonicated to homogeneity in a 37° C. solution of saline/0.5% ethanol/0.5% fatty acid-free BSA, or vehicle alone, based on appropriate time-course and dose-response preliminary experiments. Animals were then fasted for 24 h, and livers were harvested.

Measurement of ACO and CPT-I Gene Expression in Mouse Model of Fatty Liver Disease The objectives were achieved by portal vein infusion of 1-palmitoyl-2-oleoyl-sn-glycerol-3-phosphocholine (16:0/18:1-GPC) to rescue PPARα$^{-/-}$ mice from fatty liver disease or hepatic steatosis, liver tissue extraction, RT-PCR gene expression analysis of the extracted liver tissue and lipid and triglyceride assessment of the extracted liver tissue. We implanted catheters in the portal veins of mice, infused this phosphatidylcholine species or vehicle over several days, subjected animals to a fast, then isolated livers for assays of fat content as well as gene expression. Direct portal vein infusion was prompted by preliminary results showing that intraperitoneal administration of 16:0/18:1-GPC had no effect (data not shown). In additional preliminary experiments, kinetic analyses of radiolabelled phosphatidylcholine showed selective enrichment of the nucleus within minutes of portal vein administration (FIG. 12). The appearance of the catheter in the portal vein (pv-cath) is shown in FIG. 7A. Our treatment protocol is shown in FIG. 7B. After recovering from catheter placement, mice were started on a zero fat diet (ZFD) and treated with thrice-daily infusions of phosphatidylcholine or vehicle between days 4 and 9 followed by a prolonged fast. Fasting causes fatty liver in mice, an effect that is amplified in PPARα null mice. Fat staining of liver is shown in FIG. 7C and liver triglyceride quantified in FIG. 7D. Lipid content of PPARα-deficient mice was increased as compared to controls and unaffected by phosphatidylcholine infusion. Fat content was decreased in control (C57/BL6) mice with infusion of 16:0/18:1-GPC as compared to vehicle. The PPARα-dependent genes ACO and CPT-1 were increased by 16:0/18:1-GPC in control mice but not in PPARα-deficient mice (FIG. 7E). Reverse transcription to cDNA and real-time quantitative PCR were performed using previously published procedures and primer-probe sequences for ACO and CPT-1 (Chakravarthy et al., 2005). FIG. 7F shows how fatty acid synthesis, phosphatidylcholine synthesis, and PPARα signaling appear to be related based on the current findings.

REFERENCES CITED

The following references are cited throughout this disclosure. Applicant makes no statement, inferred or direct, regarding the status of these references as prior art. These references, as well as any others that are mentioned herein but not recited in this list, are referenced in their entirety and are hereby incorporated herein by reference in their entirety.

U.S. PATENT DOCUMENTS

U.S. Pat. No. 7,301,033, November 2007, Yamazaki et al.; U.S. Pat. No. 7,442,796 October 2008, Sharma et al.

FOREIGN PATENT DOCUMENTS

WO 2006-006832, January 2006, Myung et al.; WO 2004-039430, May 2004, Kurtz Seymour; EP0209038, January 1987, Bruno et al.

OTHER REFERENCES

Issemann, et al., "Activation of a member of the steroid hormone receptor superfamily by peroxisome proliferators", Nature, vol. 347, Oct. 18, 1990, pp. 645-650. cited by other.

Dreyer, et al., "Control of the Peroxisomal .beta.-Oxidation Pathway by a Novel Family of Nuclear Hormone Receptors", Cell, vol. 68, Mar. 6, 1992, pp. 879-887. cited by other.

A Unified Nomenclature System for the Nuclear Receptor Superfamily", Cell, vol. 97, Apr. 16, 1999, pp. 161-163. cited by other.

Schoonjans et al., "The peroxisome proliferator activated receptors (PPARs) and their effects on lipid metabolism and adipocyte differentiation", Biochimica et Biophysica Acta 1302, 1996, pp. 93-109. cited by other.

Willson, et al., "The PPARs: From Orphan Receptors to Drug Discovery", Journal of Medicinal Chemistry, vol. 43, No. 4, Feb. 24, 2000, pp. 527-550, cited by other.

Bensinger and Tontonoz, "Integration of metabolism and inflammation by lipid-activated nuclear receptors", Nature 454, pp. 470-477, 2008.

Barter and Rye, "Is there a role for fibrates in the management of dyslipidemia in the metabolic syndrome?", Arterioscler Thromb Vasc Biol 28, pp. 39-46, 2008.

Yki-Jarvinen, H. "Thiazolidinediones", N Engl J Med 351, pp. 1106-1118, 2004.

Riserus et al., "Activation of peroxisome proliferator-activated receptor (PPAR)delta promotes reversal of multiple metabolic abnormalities, reduces oxidative stress, and increases fatty acid oxidation in moderately obese men", Diabetes 57, pp. 332-339, 2008.

Forman et al., "Hypolipidemic drugs, polyunsaturated fatty acids, and eicosanoids are ligands for peroxisome proliferator-activated receptors alpha and delta", Proc Natl Acad Sci USA 94, pp. 4312-4317, 1997.

Kliewer et al., "Fatty acids and eicosanoids regulate gene expression through direct interactions with peroxisome proliferator-activated receptors alpha and gamma", Proc Natl Acad Sci USA 94, pp. 4318-4323, 1997.

Krey et al., "Fatty acids, eicosanoids, and hypolipidemic agents identified as ligands of peroxisome proliferator-activated receptors by coactivator-dependent receptor ligand assay", Mol Endocrinol 11, pp. 779-791, 1997.

Yu et al., "Differential activation of peroxisome proliferator-activated receptors by eicosanoids", J Biol Chem 270, pp. 23975-23983, 1995.

Akbiyik et al., "Ligand-induced expression of peroxisome proliferator activated receptor a and activation of fatty acid oxidation enzymes in fatty liver", European Journal of Clinical Investigation, 34, pp. 429-435, 2004.

Auwerx et al., "Regulation of Triglyceride Metabolism by PPARs: Fibrates and Thiazolidinediones have Distinct Effects", Journal of Atherosclerosis and Thrombosis, vol. 3, No. 2, 1996, pp. 81-89. cited by other.

Staels et al., "Role of PPAR in the Pharmacological Regulation of Lipoprotein Metabolism by Fibrates and Thiazolidinediones", Current Pharmaceutical Design, vol. 3, No. 1, 1997, pp. 1-14. cited by other.

Pineda et al., "Peroxisome proliferator-activated receptor alpha in metabolic disease, inflammation, atherosclerosis and aging", Current Opinion in Lipidology, 10, 1999, pp. 151-159. cited by other.

Vamecq et al., "Medical significance of peroxisome proliferator-activated receptors", The Lancet, vol. 354, Jul. 10, 1999, pp. 141-148. cited by other.

Willson et al., "The PPARs: From Orphan Receptors to Drug Discovery", Journal of Medicinal Chemistry, vol. 43, No. 4, Feb. 24, 2000, pp. 527-550. cited by other.

Robins et al., "PPAR.alpha. ligands and clinical trials: cardiovascular risk reduction with fibrates", Journal of Cardiovascular Risk, vol. 8, No. 4, 2001, pp. 195-201. cited by other.

Bernal-Mizrachi et al., "Dexamethasone induction of hypertension and diabetes is PPARalpha-dependent in LDL receptor-null mice", Nat Med 9, pp. 1069-1075, 2003.

Reddy et al.,"Peroxisomal beta-oxidation and peroxisome proliferator-activated receptor alpha: an adaptive metabolic system", Annu Rev Nutr 21, pp. 193-230, 2001.

Gonzalez et al., "Mechanism of Action of the Nongenotoxic Peroxisome Proliferators: Role of the Peroxisome Proliferator-Activated Receptor .alpha.", Journal of the National Center Institute, vol. 90, No. 22, Nov. 18, 1998, pp. 1702-1709. cited by other.

Fruchart, et al., "Peroxisome proliferator-activated receptor-alpha activators regulate genes governing lipoprotein metabolism, vascular inflammation and atherosclerosis", Current Opinion in Lipidology, 10, 1999, pp. 245-257. cited by other.

Ayers et al., "Continuous nucleocytoplasmic shuttling underlies transcriptional activation of PPARgamma by FABP4", Biochemistry 46, pp. 6744-6752, 2007.

Newberry et al., "Decreased hepatic triglyceride accumulation and altered fatty acid uptake in mice with deletion of the liver fatty acid-binding protein gene", J Biol Chem 278, pp. 51664-51672, 2003.

Semenkovich, C. F. "Regulation of fatty acid synthase (FAS)", Prog Lipid Res 36, pp. 43-53, 1997.

Chakravarthy et al., "New hepatic fat activates PPARalpha to maintain glucose, lipid, and cholesterol homeostasis", Cell Metab 1, pp. 309-322, 2005.

Chakravarthy et al., "Brain fatty acid synthase activates PPARalpha to maintain energy homeostasis", J Clin Invest 117, pp. 2539-2552, 2007.

Zomer et al., "Pristanic acid and phytanic acid: naturally occurring ligands for the nuclear receptor peroxisome proliferator-activated receptor α" J Lipid Res, 41(11) November 2000 pp. 1801-1807.

Fischer et al., "Peroxisome Proliferator-activated Receptor a (PPARα) Agonist Treatment Reverses PPARα Dysfunction and Abnormalities in Hepatic Lipid Metabolism in Ethanol-fed Mice", J. Biol Chem, 278 (30), pp. 27997-28004, 2003.

Seo et al., "PPAR agonists treatment is effective in a nonalcoholic fatty liver disease animal model by modulating fatty-acid metabolic enzymes", J. Gastroenterology and Hepatology, 23(1), pp. 102-108, 2008.

Haffner, S. M., "Dyslipidemia and insulin resistance are related metabolic conditions", *Am. J. Cardiol.* 83: pp. 17F-21F, 1999.

Ginsberg, H. N. and Huang, L. S., "The insulin resistance syndrome: impact on lipoprotein metabolism and. atherothrombosis." *J. Cardiovasc. Risk* 7: pp. 325-331, 2000.

Gervois et al., "Regulation of lipid and lipoprotein metabolism by PPAR activators", *Clin. Chem. Lab. Med.* 38: pp. 3-11, 2000.

Hsu et al., "Formation of lithiated adducts of glycerophosphocholine lipids facilitates their identification by electrospray ionization tandem mass spectrometry", J Am Soc Mass Spectrom 9, pp. 516-526, 1998.

Hunt et al., "Phospholipid composition of neonatal guinea pig liver and plasma: effect of postnatal food restriction", Lipids 31, pp. 489-495, 1996.

Hunt et al., "Developmental variation in whole human lung phosphatidylcholine molecular species: a comparison with guinea pig and rat", Early Hum Dev 25, pp. 157-171, 1991.

Ridgway and Lagace, "Regulation of the CDP-choline pathway by sterol regulatory element binding proteins involves transcriptional and post-transcriptional mechanisms", Biochem J 372, pp. 811-819, 2003.

Krylova et al. "Structural analyses reveal phosphatidyl inositols as ligands for the NR5 orphan receptors SF-1 and LRH-1", Cell 120, pp. 343-355, 2005.

Guo et al., "Enzymatic modification of phospholipids for functional applications and human nutrition", *Biotechnology Advances* 23, pp. 203-259, 2005.

Weihrauch and Son, "The phospholipids content of foods", J Am Oil Chem Soc 1983; 60(12); pp. 1971-1978. cited by other.

van Nieuwenhuyzen. "Lecithin production and properties", J Am Oil Chem Soc 1976; 53: pp. 425-427. cited by other.

Zhao et al., "Identification and characterization of a major liver lysophosphatidylcholine acyltransferase", J Biol Chem 283, pp. 8258-8265, 2008.

Billas et al., "Crystal structure of the ligand-binding domain of the ultraspiracle protein USP, the ortholog of retinoid X receptors in insects", J Biol Chem 276, pp. 7465-7474, 2001.

Clayton et al., "The structure of the ultraspiracle ligand-binding domain reveals a nuclear receptor locked in an inactive conformation", Proc Natl Acad Sci USA 98, pp. 1549-1554, 2001.

Li et al., Crystallographic identification and functional characterization of phospholipids as ligands for the orphan nuclear receptor steroidogenic factor-1", Mol Cell 17, pp. 491-502, 2005.

Ortlund et al., "Modulation of human nuclear receptor LRH-1 activity by phospholipids and SHP", Nat Struct Mol Biol 12, pp. 357-363, 2005.

Forman, B. M., "Are those phospholipids in your pocket?" Cell Metab 1, pp. 153-155, 2005.

Davies et al. (2001). "Oxidized alkyl phospholipids are specific, high affinity peroxisome proliferator-activated receptor gamma ligands and agonists", J Biol Chem 276, pp. 16015-16023, 2001.

Delerive et al., "Oxidized phospholipids activate PPARalpha in a phospholipase A2-dependent manner", FEBS Lett 471, pp. 34-38, 2000.

Lee et al., "Role for peroxisome proliferator-activated receptor alpha in oxidized phospholipid-induced synthesis of monocyte chemotactic protein-1 and interleukin-8 by endothelial cells", Circ Res 87, pp. 516-521, 2000.

Straus and Glass, "Anti-inflammatory actions of PPAR ligands: new insights on cellular and molecular mechanisms", Trends Immunol 28, pp. 551-558, 2007.

Cuzzocrea et al., "Role of endogenous and exogenous ligands for the peroxisome proliferators activated receptors alpha (PPARalpha) in the development of inflammatory bowel disease in mice", Lab Invest 84, pp. 1643-1654, 2004.

Li et al., "The ratio of phosphatidylcholine to phosphatidylethanolamine influences membrane integrity and steatohepatitis", Cell Metab 3, pp. 321-331, 2006.

Stremmel et al., "Phosphatidylcholine for steroid-refractory chronic ulcerative colitis: a randomized trial" pp. Ann Intern Med 147, pp. 603-610, 2007.

Treede et al., "Anti-inflammatory effects of phosphatidylcholine", J Biol Chem 282, pp. 27155-27164, 2007.

Shah et al., "Peroxisome proliferator-activated receptor alpha regulates a microRNA-mediated signaling cascade responsible for hepatocellular proliferation", Mol Cell Biol 27, pp. 4238-4247, 2007.

Tanaka et al., "PPARalpha activation is essential for HCV core protein-induced hepatic steatosis and hepatocellular carcinoma in mice", J Clin Invest 118, pp. 683-694, 2008.

Panigrahy et al., "PPARalpha agonist fenofibrate suppresses tumor growth through direct and indirect angiogenesis inhibition", Proc Natl Acad Sci USA 105, pp. 985-990, 2008.

Henry, S. M., and Hodge, L. D. (1983). "Evidence for a unique profile of phosphatidylcholine synthesis in late mitotic cells", J Cell Biol 97, pp. 166-172, 1983.

Hunt et al., "Highly saturated endonuclear phosphatidylcholine is synthesized in situ and colocated with CDP-choline pathway enzymes", J Biol Chem 276, pp. 8492-8499, 2001.

Hsu and Turk, Electrospray ionization/tandem quadrupole mass spectrometric studies on phosphatidylcholines: the fragmentation processes. J Am Soc Mass Spectrom 14, pp. 352-363, 2003.

Hsu et al., Characterization of alkylacyl, alk-1-enylacyl and lyso subclasses of glycerophosphocholine by tandem quadrupole mass spectrometry with electrospray ionization. J Mass Spectrom 38, pp. 752-763, 2003.

Hsu et al., "Formation of lithiated adducts of glycerophosphocholine lipids facilitates their identification by electrospray ionization tandem mass spectrometry", J Am Soc Mass Spectrom 9, pp. 516-526, 1998.

Hsu and Turk, "Structural determination of sphingomyelin by tandem mass spectrometry with electrospray ionization", J Am Soc Mass Spectrom 11, pp. 437-449, 2000.

Nowatzke et al., "Mass spectrometric evidence that agents that cause loss of Ca2+ from intracellular compartments induce hydrolysis of arachidonic acid from pancreatic islet membrane phospholipids by a mechanism that does not require a rise in cytosolic Ca2+ concentration", Endocrinology 139, pp. 4073-4085, 1998.

Lodhi et al., "Gapex-5, a Rab31 guanine nucleotide exchange factor that regulates Glut4 trafficking in adipocytes", Cell Metab 5, pp. 59-72, 2007.

Pioszak et al., "Molecular recognition of parathyroid hormone by its G protein-coupled receptor", Proc Natl Acad Sci USA 105, pp. 5034-5039, 2008.

Li et al., "Crystallographic identification and functional characterization of phospholipids as ligands for the orphan nuclear receptor steroidogenic factor-1", Mol Cell 17, pp. 491-502, 2005.

Shi et al., "The peroxisome proliferator-activated receptor delta, an integrator of transcriptional repression and nuclear receptor signaling", Proc Natl Acad Sci USA 99, pp. 2613-2618, 2002.

Kent, C., "Regulatory enzymes of phosphatidylcholine biosynthesis: a personal perspective", Biochim Biophys Acta 1733, pp. 53-66, 2005.

Henneberry et al., "The major sites of cellular phospholipid synthesis and molecular determinants of fatty Acid and lipid head group specificity", Mol Biol Cell 13, pp. 3148-3161, 2002.

Strubbe et al., "Hepatic portal vein cannulation for infusion and blood sampling in freely moving rats", Physiol Behav 65, pp. 885-887, 1999.

Tzagournis, M. "Triglycerides in clinical medicine; A review", American Journal of Clinical Nutrition, Vol 31, pp. 1437-1452, 1978.

Wiser and Schweiger, "Increased sensitivity in antigen detection during immunoblot analysis resulting from antigen enrichment via immunoprecipitation", Analytical Biochemistry, 155(1), pp. 71-77, 1986.

Benthem, L., Keizer, K., Wiegman, C. H., de Boer, S. F., Strubbe, J. H., Steffens, A. B., Kuipers, F., and Scheurink, A. (2000). Excess portal venous long-chain fatty acids induce syndrome X via HPA axis and sympathetic activation. Am J Physiol Endocrinol Metab 279, E1286-E1293.

Bernal-Mizrachi, C., Weng, S., Feng, C., Finck, B. N., Knutsen, R. H., Leone, T. C., Coleman, T., Mecham, R. P., Kelly, D. P., and Semenkovich, C. F. (2003). Dexamethasone induction of hypertension and diabetes is PPARalpha-dependent in LDL receptor-null mice. Nat Med 9, 1069-1075.

Cantafora, A., Masella, R., Angelico, M., Gandin, C., Blount, R. J., and Peterson, S. W. (1992). Effect of intravenous polyunsaturated phosphatidylcholine infusion on insulin receptor processing and lipid composition of erythrocytes in patients with liver cirrhosis. Eur J Clin Invest 22, 777-782.

Chakravarthy, M. V., Pan, Z., Zhu, Y., Tordjman, K., Schneider, J. G., Coleman, T., Turk, J., and Semenkovich, C. F. (2005). "New" hepatic fat activates PPARalpha to maintain glucose, lipid, and cholesterol homeostasis. Cell Metab 1, 309-322.

Grekin, R. J., Vollmer, A. P., and Sider, R. S. (1995). Pressor effects of portal venous oleate infusion: a proposed mechanism for obesity hypertension. Hypertension 26, 193-198.

Hardman, J. G., Limbird, L. E., and Gilman, A. G. E. (2001). Goodman & Gilman's The Pharmacological Basis of Therapeutics (McGraw Hill).

Hsu, F. F., Bohrer, A., and Turk, J. (1998). Formation of lithiated adducts of glycerophosphocholine lipids facilitates their identification by electrospray ionization tandem mass spectrometry. J Am Soc Mass Spectrom 9, 516-526.

Mansbach, C. M., and Dowell, R. F. (1993). Portal transport of long acyl chain lipids: effect of phosphatidylcholine and low infusion rates. Am J Physiol 264, G1082-G1089.

Shi, Y., Hon, M., and Evans, R. M. (2002). The peroxisome proliferator-activated receptor delta, an integrator of transcriptional repression and nuclear receptor signaling. Proc Natl Acad Sci USA 99, 2613-2618.

Stremmel, W., Ehehalt, R., Autschbach, F., and Karner, M. (2007). Phosphatidylcholine for steroid-refractory chronic ulcerative colitis: a randomized trial. Ann Intern Med 147, 603-610.

Tordjman, K., Standley, K. N., Bernal-Mizrachi, C., Leone, T. C., Coleman, T., Kelly, D. P., and Semenkovich, C. F. (2002). PPARalpha suppresses insulin secretion and induces UCP2 in insulinoma cells. J Lipid Res 43, 936-943.

Treede, I., Braun, A., Sparla, R., Kuhnel, M., Giese, T., Turner, J. R., Anes, E., Kulaksiz, H., Fullekrug, J., Stremmel, W., et al. (2007). Anti-inflammatory effects of phosphatidylcholine. J Biol Chem 282, 27155-27164.

---

What is claimed is:

1. A method of treating a peroxisome proliferator-activated receptor alpha (PPARα)-related liver disorder, lowering triglyceride levels, and/or elevating high density lipoprotein levels in a mammal, said method comprising administering a therapeutically effective amount of 1-palmitoyl-2-oleoyl-sn-glycerol-3-phosphocholine (16:0/18:1-GPC) to said mammal, wherein the therapeutically effective amount is at least 5 mg of 1-palmitoyl-2-oleoyl-sn-glycerol-3-phosphocholine (16:0/18:1-GPC) per kilogram of body weight of the mammal.

2. The method of claim 1 wherein the mammal is a human.

3. The method of claim 2, wherein the PPARα-related liver disorder is fatty liver disease.

4. The method of claim 2, wherein the 1-palmitoyl-2-oleoyl-sn-glycerol-3-phosphocholine (16:0/18:1-GPC) is an isolated form.

5. The method of claim 2, wherein the 1-palmitoyl-2-oleoyl-sn-glycerol-3-phosphocholine (16:0/18:1-GPC) is in the form of a 1-palmitoyl-2-oleoyl-sn-glycerol-3-phosphocholine (16:0/18:1-GPC)-chaperone complex.

6. The method of claim 2, further comprising a step of quantifying the level of triglyceride in the liver as a means of monitoring the efficacy of administering said 1-palmitoyl-2-oleoyl-sn-glycerol-3-phosphocholine (16:0/18:1-GPC).

7. The method of claim 2, wherein the 1-palmitoyl-2-oleoyl-sn-glycerol-3-phosphocholine (16:0/18:1-GPC) is administered as a pharmaceutical composition.

8. The method of claim 7, wherein said pharmaceutical composition further comprises a pharmaceutically acceptable carrier, excipient, or diluent.

* * * * *